(12) United States Patent
Makino et al.

(10) Patent No.: US 7,321,831 B2
(45) Date of Patent: Jan. 22, 2008

(54) NUCLEIC ACID FRAGMENT-FIXED ELECTRODE AND ITS USE

(75) Inventors: Yoshihiko Makino, Saitama (JP); Yoshihiko Abe, Saitama (JP)

(73) Assignee: Fujifilm Corporation, Tokyo (JP)

( * ) Notice: Subject to any disclaimer, the term of this patent is extended or adjusted under 35 U.S.C. 154(b) by 409 days.

(21) Appl. No.: 10/231,242

(22) Filed: Aug. 30, 2002

(65) Prior Publication Data

US 2003/0152958 A1 Aug. 14, 2003

(30) Foreign Application Priority Data

Sep. 3, 2001 (JP) .............................. 2001-265482

(51) Int. Cl.
 *G01N 33/48* (2006.01)
 *C12Q 1/00* (2006.01)
 *C12Q 1/68* (2006.01)
 *G01N 33/00* (2006.01)
 *G06F 19/00* (2006.01)

(52) U.S. Cl. .................. 702/19; 435/4; 435/6; 702/20; 702/27

(58) Field of Classification Search .................... 435/6, 435/7, 8; 702/19; 427/2
See application file for complete search history.

(56) References Cited

U.S. PATENT DOCUMENTS

| 5,776,672 | A | | 7/1998 | Hashimoto et al. | |
|---|---|---|---|---|---|
| 5,912,126 | A | * | 6/1999 | Darzynkiewicz et al. | ...... 435/6 |
| 5,942,397 | A | | 8/1999 | Tarlov et al. | |
| 6,127,127 | A | * | 10/2000 | Eckhardt et al. | ............... 435/6 |
| 6,127,129 | A | | 10/2000 | Corn et al. | |
| 6,368,807 | B2 | | 4/2002 | Makino et al. | |
| 6,864,055 | B2 | * | 3/2005 | Makino et al. | ................. 435/6 |
| 2001/0024788 | A1 | * | 9/2001 | Hashimoto | ..................... 435/6 |
| 2001/0053522 | A1 | * | 12/2001 | Makino et al. | ................. 435/6 |

* cited by examiner

*Primary Examiner*—Ram R. Shukla
*Assistant Examiner*—Eric S DeJong
(74) *Attorney, Agent, or Firm*—Birch, Stewart, Kolasch & Birch, LLP

(57) ABSTRACT

It is an object of the present invention to provide a nucleic acid fragment-fixed electrode wherein a probe nucleic acid fragment is fixed on the electrode stably and in an amount-controlled manner. The present invention provides a nucleic acid fragment-fixed electrode wherein a nucleic acid fragment is fixed on the surface of a multi-component self-assembled monolayer of two or more different components which is formed on the electrode, by a covalent bond via a bifunctional linking molecule.

14 Claims, 1 Drawing Sheet

[Fig. 1]
[a]
$(Q-R-J^1) = (Q-R-J^2)$
[b]
$(Q-R-J^1) < (Q-R-J^2)$
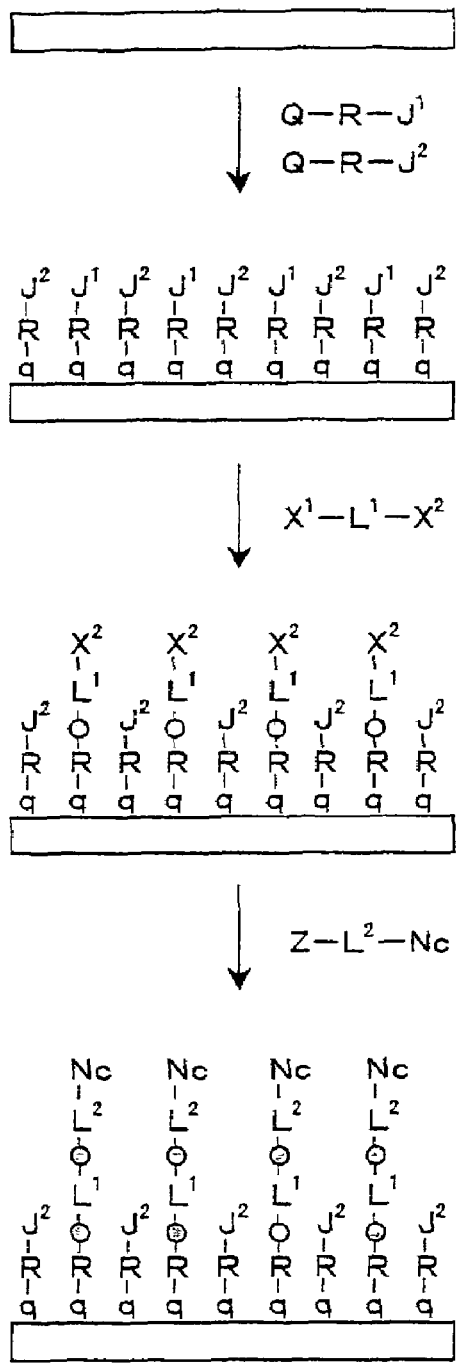
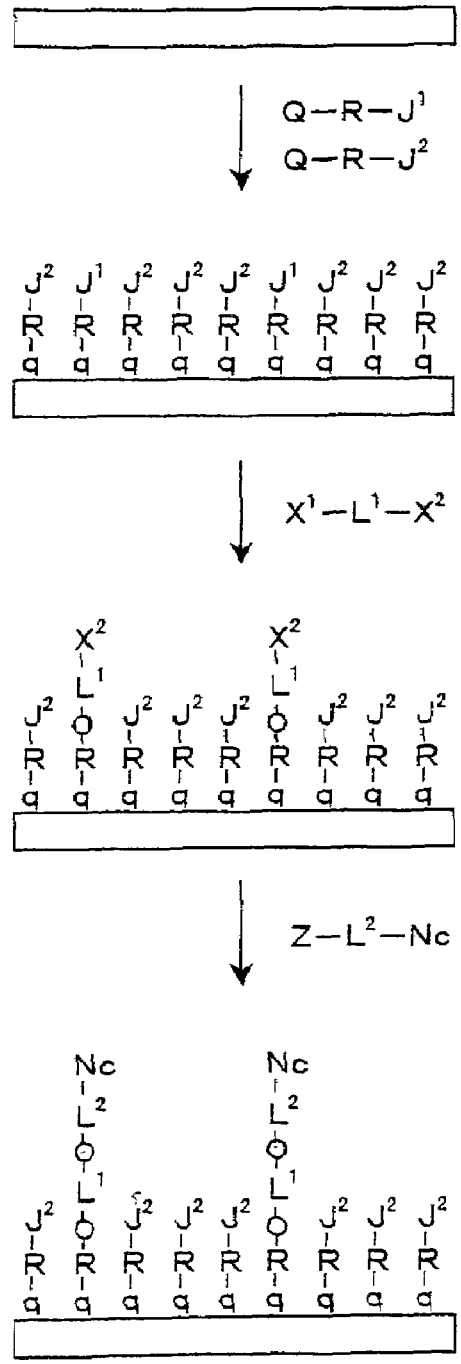

NUCLEIC ACID FRAGMENT-FIXED ELECTRODE AND ITS USE

TECHNICAL FIELD

The present invention relates to a detection tool useful for the detection of a target nucleic acid fragment having a specific nucleotide sequence, which tool can be effectively used for clinical examination of infectious diseases caused by viruses, bacteria or the like and for the examination of genetic diseases based on genetic traits of individuals. In particular, the present invention relates to a nucleic acid fragment-fixed electrode which can be advantageously used in a method of electrochemically detecting a target nucleic acid fragment. More particularly, the present invention relates to an array type detection tool useful for the detection of a target nucleic acid fragment, a method of producing the tool, and an electrochemical detection method using the array type detection tool. In the array detection tool, electrodes are arrayed on the surface of a substrate, and probe nucleic acid fragments complementary to the target nucleic acid are fixed on the electrode.

BACKGROUND ART

Advances are being made in technologies to efficiently analyze the genetic functions of a variety of living organisms. To analyze the expression of their genes or the nucleotide sequences of the genes, a detection tool called a DNA chip is used, in which a number of nucleic acid fragments are fixed on the surface of a solid support. The nucleic acid fragments bound or fixed on the surface of the solid support are also called probe nucleic acid fragments. A typical DNA chip is a microarray wherein a number of probe nucleic acid fragments are arrayed and fixed on a solid support such as a slide glass. The DNA chip related technologies relating to the production of the DNA chip and its use are believed to be applicable also to the detection of biomolecules other than DNA. Thus, there are expectations that such technologies will provide new means for the research of new drugs and the development of a method for diagnosing and preventing diseases.

A breakthrough in the progress of DNA-chip related technologies was achieved when a method of determining the nucleotide sequence of nucleic acid fragments based on hybridization with an oligonucleotid was developed. Even though this method can overcome the limitations in the methods of determining nucleotide sequences using gel electrophoresis, it was only later that the hybridization method came to be used for practical purposes.

Then, a DNA chip of the above-described structure and technologies for the production thereof were developed, and it became possible to examine the expression, mutation, polymorphism or the like of a gene efficiently in a short time. Specifically, a target nucleic acid fragment showing complementarity with the probe nucleic acid fragments on the produced DNA chip is generally detected by utilizing hybridization between the probe nucleic acid fragment on the DNA chip and the target nucleic acid fragment.

One method for detecting hybridization between the probe nucleic acid fragment on the DNA chip and the target nucleic acid fragment is a method of labeling the target nucleic acid fragment with a detectable molecule in advance. Most generally, the target nucleic acid is labeled with a fluorescent dye as the labeling molecule.

Following the hybridization process, fluorescence emitted from the surface of the DNA chip is measured to detect only those locations (spots) on the DNA chip where hybridization between the probe nucleic acid fragments and the target nucleic acid fragment occurred. It is also possible to determine the existing amount of target nucleic acid fragments on the basis of the intensity of the measured fluorescence. However, this method requires that the target nucleic acid be labeled by the fluorescent dye in advance. The measurement of the fluorescence emitted from the surface of the DNA chip has a disadvantage in that it is not a simple method, since a large-sized apparatus is required and the measurement takes time.

Another method of detecting hybridization between the probe nucleic acid fragment on the DNA chip and the target nucleic acid fragment is known from Japanese Patent No.2573443. This method detects hybridization by electrochemical measurement, using a double-stranded nucleic acid fragment recognizing substance which has an electrochemical activity and can bind specifically to the double-stranded nucleic acid. This method is simpler and superior in that it does not require the target nucleic acid fragment to be labeled in advance and in that the electrochemical measurement can be performed in a small-sized apparatus in a short time. The method is therefore expected to provide a new hybridization detecting means which can be used in the field of clinical examination, for example.

As described above, in the detection methods by utilizing hybridization between the probe nucleic acid fragment on the DNA chip and the target nucleic acid fragment, the reproducibility of the detection of the target nucleic acid fragment is dependent on whether or not the probe nucleic acid fragments are fixed on the surface of the solid support in a stable manner. Further, the fixing density of the probe nucleic acid fragments on the solid support surface (i.e., the amount of the same kind of probe nucleic acid fragments fixed per unit area) determines the sensitivity and limit with which the target nucleic acid can be detected. Thus, in order to realize a practical method of detecting a target nucleic acid by using a DNA chip, a technology must be provided for fix a number of probe nucleic acid fragments on the surface of a solid support in a stable and density-controlled manner.

A method of producing a DNA chip is known whereby an oligonucleotide is synthesized directly on the solid support surface ("on-chip method"). Another method involves the bonding and fixing of probe nucleic acid fragments prepared in advance on the surface of a solid support. A typical on-chip method is based on the use of a combination of a protection group which is selectively removed by irradiation of light, and photolithography and solid-phase synthesizing techniques which are used in the production of semiconductor, whereby an oligonucleotide is selectively synthesized in a predetermined small matrix region.

As methods of binding or fixing a probe nucleic acid fragment prepared in advance on the surface of a solid support, the following are known depending on the type of the probe nucleic acid fragment and the solid support.

(1) In the case where the fixed probe nucleic acid fragment is cDNA (complementary DNA synthesized by using mRNA as a template) or a PCR product (a DNA fragment obtained by amplifying cDNA by PCR), the cDNA or PCR product is spotted onto the surface of a solid support treated with a poly-cationic compound (e.g. polylysine or polyethylene-imine) so that the cDNA or PCR product is bound to the support via electrostatic bonding by utilizing the electric charge of the probe nucleic acid fragment. The treatment of the surface of the solid support may be performed by a method utilizing a silane coupling agent containing an amino group, aldehyde group, epoxy group or the like. In the surface treatment using such a silane coupling agent, the amino group, aldehyde group or the like are fixed to the solid support surface via a covalent bond, so that the cDNA or PCR product can be fixed to the support surface more stably than in the case of surface treatment with a poly-cationic compound.

As a variation of the above method utilizing the charge of the probe nucleic acid fragment, a method has been reported where a PCR product modified with an amino group is suspended in SSC (buffer solution of standard sodium chloride/citrate), and the suspension is spotted onto the surface of sililated slide glass and, after incubation, a processing with sodium borohydride and a heat processing are successively performed. In this method, however, the probe nucleic acid fragment cannot be fixed with sufficient stability.

(2) In the case where the fixed probe nucleic acid fragment is a synthetic oligonucleotide, initially an oligonucleotide to which a reactive group has been introduced is synthesized. The oligonucleotide is then spotted onto a solid support whose surface has been treated such that a reactive group is formed, so that the oligonucleotide is bound and fixed to the solid support surface via covalent bonding. For example, in one method, an amino-group introduced oligonucleotide is reacted with a slide glass onto a surface of which an amino group has been introduced, under the presence of PDC (p-phenylene diisothiocyanate). In another method, an aldehyde-group introduced oligonucleotide is reacted with the slide glass. These two methods are advantageous over the fixing method (1) based on static bonding where electric charge of the DNA fragment is utilized, in that the oligonucleotide is fixed to the surface of the solid support in a stable manner. However, these methods have problems. For example, in the method involving the presence of PDC, the reaction between PDC and the amino-group introduced oligonucleotide is slow. In the method utilizing the aldehyde-group introduced oligonucleotide, the stability of the Schiff base which is a reaction product, is low (and therefore hydrolysis is likely to occur).

A technique has been proposed recently in which an oligonucleotide analog called PNA (peptide nucleic acid) is used instead of an oligonucleotide or polynucleotide (including synthetic oligonucleotide, DNA fragment and RNA fragment) as the probe nucleic acid fragment in a DNA chip. A method of fixing the PNA to the solid support via covalent bonding is known from Japanese Patent Application Laid-Open (kokai) No. 11-332595 where the combination of avidin and biotin is used. This publication discloses the use of a surface plasmon resonance (SPR) sensor as the solid support.

SUMMARY OF THE INVENTION

It is an object of the present invention to provide a nucleic acid fragment-fixed electrode wherein a probe nucleic acid fragment is fixed on the electrode stably and in an amount-controlled manner, a method of producing the nucleic acid fragment-fixed electrode, and a method of electrochemically detecting a target nucleic acid by using the nucleic acid fragment-fixed electrode.

After extensive research and analysis to achieve the above object of the invention, the present inventors have found that a target nucleic acid fragment can be efficiently detected by using a nucleic acid fragment-fixed electrode wherein a nucleic acid fragment is fixed by covalent bond via a bifunctional linking molecule onto the surface of a multi-component self-assembled monolayer which is formed on the electrode and is composed of two or more different components. The inventors have also found that the amount of the nucleic acid fragment that binds, via the bifunctional linking molecule, to the surface of the multi-component self-assembled monolayer formed on the electrode can be controlled by changing the molar ratio of the molecules used when the multi-component self-assembled monolayer is formed. The present invention has been completed based on these findings.

Thus, according to the present invention, there is provided a nucleic acid fragment-fixed electrode wherein a nucleic acid fragment is fixed on the surface of a multi-component self-assembled monolayer of two or more different components which is formed on the electrode, by a covalent bond via a bifunctional linking molecule.

Preferably in the nucleic acid fragment-fixed electrode of the present invention, the monolayer is composed of at least two components represented by the following formula (1) with the type of $J''$ being different:

$$q''\text{-}R''\text{-}J'' \tag{1}$$

wherein $q''$ represents a group which is chemically bound to or adsorbed on the electrode, $R''$ represents s a linking group, $J''$ represents different functional groups of n types, and n represents an integer of 2 or more, and in the components of formula (1) of n types, $q''$ and $R''$ may be identical or different from each other, and $J''$ are different from each other; and the bifunctional linking molecule is represented by the following formula (2):

$$X^1\text{-}L^1\text{-}X^2 \tag{2}$$

wherein $X^1$ represents a reactive group which forms a covalent bond with at least one type of the functional group $J''$ in the above formula (1), $X^2$ represents a reactive group which forms a covalent bond with a functional group Z in the following formula (3), and $L^1$ represents a linking group; and the nucleic acid fragment is represented by the following formula (3):

$$Z\text{-}L^2\text{-}Nc \tag{3}$$

wherein Z represents a reactive group which forms a covalent bond with the reactive group $X^2$ in the above formula (2), Nc represents a nucleic acid fragment, and $L^2$ represents a linking group.

Preferably, the multi-component self-assembled monolayer formed on the electrode is composed of at least two different components represented by the following formula (4):

$$q^1\text{-}R^1\text{-}J^1 \tag{4}$$

wherein $q^1$ represents a group which is chemically bound to or adsorbed on the electrode, $R^1$ represents a linking group, $J^1$ represents a reactive group which forms a covalent bond with the reactive group $X^1$ in the above formula (2); and the following formula (5):

$$q^2\text{-}R^2\text{-}J^2 \tag{5}$$

wherein $q^2$ represents a group which is chemically bound to or adsorbed on the electrode, $R^2$ represents a linking group, and $J^2$ represents a functional group which does not react or has low reactivity with the reactive groups $X^1$ and $X^2$ in the above formula (2).

Preferably, the electrode is made of gold.

Preferably, the multi-component self-assembled monolayer is composed of two different components of an alkanethiol having a terminal amino group and having 3 to 16 carbon atoms and an alkanethiol having a terminal hydroxyl group and having 3 to 16 carbon atoms.

Preferably, the bifunctional linking molecule is a disulfone compound represented by the following formula (6):

$$X^1-SO_2-L^3-SO_2-X^2 \qquad (6)$$

wherein $X^1$ and $X^2$ represent independently $-CR^1=CR^2R^3$ or $-CHR^1-CR^2R^3Y$; $R^1$, $R^2$ and $R^3$ represent independently an atom or a group selected from the group consisting of a hydrogen atom, an alkyl group having 1 to 6 carbon atoms, an aryl group having 6 to 20 carbon atoms, and an aralkyl group having 7 to 26 carbon atoms in total which has an alkyl chain having 1 to 6 carbon atoms; Y represents an atom or a group selected from the group consisting of a halogen atom, $-OSO_2R^{11}$, $-OCOR^{12}$, $-OSO_3M$ and quaternary pyridinium group; $R^{11}$ represents a group selected from the group consisting of an alkyl group having 1 to 6 carbon atoms, an aryl group having 6 to 20 carbon atoms, and an aralkyl group having 7 to 26 carbon atoms in total which has an alkyl chain having 1 to 6 carbon atoms; $R^{12}$ represents a group selected from the group consisting of an alkyl group having 1 to 6 carbon atoms, and a halogenated alkyl group having 1 to 6 carbon atoms; M represents an atom or a group selected from the group consisting of a hydrogen atom, alkaline metal atom and ammonium group; and $L^3$ represents a linking group.

Preferably, the nucleic acid fragment is either a DNA fragment modified at the terminal with an amino acid group, which is represented by the following formula (7):

$$NH_2-L^4-DNA \qquad (7)$$

wherein $L^4$ represents a linking group; or
a PNA fragment having a terminal lysine residue, which is represented by the following formula (8):

$$Lys-PNA \qquad (8)$$

wherein Lys represents a lysine residue.

According to another aspect of the present invention, there is provided a method for producing a nucleic acid fragment-fixed electrode wherein a nucleic acid fragment is fixed on the surface of a multi-component self-assembled monolayer of two or more different components which is formed on the electrode, by a covalent bond via a bifunctional linking molecule, the method comprising at least the steps of:

(a) forming a multi-component self-assembled monolayer on an electrode by contacting the electrode with at least two components represented by the following formula (1) with the type of $J^n$ being different:

$$q^n-R^n-J^n \qquad (1)$$

wherein $q^n$ represents a group which is chemically bound to or adsorbed on the electrode, $R^n$ represents s a linking group, $J^n$ represents different functional groups of n types, and n represents an integer of 2 or more, and in the components of formula (1) of n types, $q^n$ and $R^n$ may be identical or different from each other, and $J^n$ are different from each other; and then removing the components which were not chemically bound to or adsorbed on the electrode;

(b) introducing a reactive group $X^2$ onto the surface of the multi-component self-assembled monolayer by contacting the electrode obtained in step (a) on which the multi-component self-assembled monolayer is formed with a bifunctional linking molecule represented by the following formula (2):

$$X^1-L^1-X^2 \qquad (2)$$

wherein $X^1$ represents a reactive group which forms a covalent bond with at least one type of functional group $J^n$ in the above formula (1), $X^2$ represents a reactive group which forms a covalent bond with a functional group Z in the following formula (3), and $L^1$ represents a linking group; and then removing the components which did not form a covalent bond with the reactive group $J^n$ on the multi-component self-assembled monolayer; and (c) binding a nucleic acid fragment partially to the surface of the multi-component self-assembled monolayer by contacting the electrode obtained in step (b) having a multi-component self-assembled monolayer on which the reactive group $X^2$ is introduced with a nucleic acid fragment represented by the following formula (3):

$$Z-L^2-Nc \qquad (3)$$

wherein Z represents a reactive group which forms a covalent bond with the reactive group $X^2$ in the above formula (2), Nc represents a nucleic acid fragment, and $L^2$ represents a linking group; and then removing the unwanted components which did not form a covalent bond with the reactive group $X^2$ introduced onto the multi-component self-assembled monolayer.

Preferably, in the step of forming the multi-component self-assembled monolayer on the electrode, the multi-component self-assembled monolayer is formed on the electrode by contacting the electrode with a mixture solution containing at least two different components represented by the following formula (4):

$$q^1-R^1-J^1 \qquad (4)$$

wherein $q^1$ represents a group which is chemically bound to or adsorbed on the electrode, $R^1$ represents a linking group, $J^1$ represents a reactive group which forms a covalent bond with the reactive group $X^1$ in the above formula (2); and the following formula (5):

$$q^2-R^2-J^2 \qquad (5)$$

wherein $q^2$ represents a group which is chemically bound to or adsorbed on the electrode, $R^2$ represents a linking group, and $J^2$ represents a functional group which does not react or has low reactivity with the reactive groups $X^1$ and $X^2$ in the above formula (2); and then removing the components which were not chemically bound to or adsorbed on the electrode; and further the reactive group $X^2$ is partially introduced onto the surface of the multi-component self-assembled monolayer by contacting the electrode with the bifunctional linking molecule of the above formula (2) and then removing the components which did not form a covalent bond with the reactive group $J^n$ on the multi-component self-assembled monolayer.

Preferably, the amount of the nucleic acid fragment bound via the bifunctional linking molecule to the surface of the multi-component self-assembled monolayer formed on the electrode is controlled by changing the molar ratio of the molecule ($q^1-R^1-J^1$) represented by formula (4) and the molecule ($q^2-R^2-J^2$) represented by formula (5) in the mixture solution which is brought into contact with the electrode.

Preferably, the molar ratio of the molecule ($q^1$-$R^1$-$J^1$) represented by formula (4) and the molecule ($q^2$-$R^2$-$J^2$) represented by formula (5) in the mixture solution to be contacted with the electrode is in the range of from 1:1 to 1:1000.

Preferably, the electrode is made of gold.

Preferably, the molecule ($q^1$-$R^1$-$J^1$) represented by formula (4) is an alkanethiol having a terminal amino group and having 3 to 16 carbon atoms, and the molecule ($q^2$-$R^2$-$J^2$) represented by formula (5) is an alkanethiol having a terminal hydroxyl group and having 3 to 16 carbon atoms.

Preferably, the bifunctional linking molecule is a disulfone compound represented by the following formula (6):

$$X^1\text{—}SO_2\text{-}L^3\text{-}SO_2\text{—}X^2 \quad (6)$$

wherein $X^1$ and $X^2$ represent independently —$CR^1$=$CR^2R^3$ or —$CHR^1$—$CR^2R^3Y$; $R^1$, $R^2$ and $R^3$ represent independently an atom or a group selected from the group consisting of a hydrogen atom, an alkyl group having 1 to 6 carbon atoms, an aryl group having 6 to 20 carbon atoms, and an aralkyl group having 7 to 26 carbon atoms in total which has an alkyl chain having 1 to 6 carbon atoms; Y represents an atom or a group selected from the group consisting of a halogen atom, —$OSO_2R^{11}$, —$OCOR^2$, —$OSO_3M$ and quaternary pyridinium group; $R^{11}$ represents a group selected from the group consisting of an alkyl group having 1 to 6 carbon atoms, an aryl group having 6 to 20 carbon atoms, and an aralkyl group having 7 to 26 carbon atoms in total which has an alkyl chain having 1 to 6 carbon atoms; $R^{12}$ represents a group selected from the group consisting of an alkyl group having 1 to 6 carbon atoms, and a halogenated alkyl group having 1 to 6 carbon atoms; M represents an atom or a group selected from the group consisting of a hydrogen atom, alkaline metal atom and ammonium group; and $L^3$ represents a linking group.

Preferably, the nucleic acid fragment is either a DNA fragment modified at the terminal with an amino acid group which is represented by the following formula (7):

$$NH_2\text{-}L^4\text{-DNA} \quad (7)$$

wherein $L^4$ represents a linking group; or a PNA fragment having a terminal lysine residue which is represented by the following formula (8):

$$Lys\text{-PNA} \quad (8)$$

wherein Lys represents a lysine residue.

According to another aspect of the present invention, there is provided a method of electrochemically detecting a target nucleic acid fragment which comprises the steps of:

(a) contacting the nucleic acid fragment-fixed electrode according to any of claims 1 to 7 or the nucleic acid fragment-fixed electrode produced by the method according to any of claims 7 to 14 with a sample solution containing the target nucleic acid fragment, and hybridizing the target nucleic acid fragment to the probe nucleic acid fragment which is fixed on said nucleic acid fragment-fixed electrode;

(b) contacting the nucleic acid fragment-fixed electrode to which the target nucleic acid fragment has been hybridized, with a molecule which has an electrochemical activity and can specifically bind to a double-strand nucleic acid formed by hybridization; and (c) conducting an electrochemical measurement via the nucleic acid fragment-fixed electrode.

Preferably, the molecule which has an electrochemical activity and can specifically bind to a double-strand nucleic acid formed by hybridization is an intercalater.

BRIEF DESCRIPTION OF THE DRAWINGS

FIG. 1 schematically illustrates the method of controlling the amount (density) of a nucleic acid fragment fixed on the surface of a multi-component self-assembled monolayer via a bifunctional linking molecule, where the amount (density) of the bifunctional molecule introduced onto the surface of the multi-component self-assembled monolayer is controlled by controlling the ratio of the components of the multi-component self-assembled monolayer.

DETAILED DESCRIPTION OF PREFERRED EMBODIMENTS

Preferred embodiments of the present invention will be hereafter described in detail.

The present invention relates to a nucleic acid fragment-fixed electrode, a method of producing the electrode, and a method of electrochemically detecting a target nucleic acid by using the electrode. In the nucleic acid fragment-fixed electrode, a probe nucleic acid fragment is fixed to the surface of a multi-component self-assembled monolayer formed on the electrode, by covalent bonding via a bifunctional linking molecule.

The multi-component self-assembled monolayer in the nucleic acid fragment-fixed electrode according to the present invention is preferably composed of at least two components, one being a self-assembled monolayer component having a terminal reactive group which reacts with at least one of reactive groups of the bifunctional linking molecule to thereby form a covalent bond, by which molecule a nucleic acid fragment is bound to the surface of the multi-component self-assembled monolayer, and the other being a self-assembled monolayer component having a terminal reactive group which does not react or has low reactivity with either reactive group of the bifunctional linking molecule. The nucleic acid fragment to be fixed is preferably modified at the terminal with a reactive group which reacts with at least one of reactive groups of the bifunctional linking molecule to form a covalent bond.

Further, in the nucleic acid fragment-fixed electrode according to the present invention, the electrode is preferably made of gold. The bifunctional linking molecule is preferably a disulfone compound. The multi-component self-assembled monolayer is preferably composed of at least two components of alkanethiol (number of carbon atoms 3 to 16) having a terminal amino group and alkanethiol (number of carbon atoms 3 to 16) having a terminal hydroxyl group. The nucleic acid fragment to be fixed is preferably a DNA fragment modified at the terminal with an amino group via a linking group, or a PNA fragment having a terminal lysine residue.

It is preferable that, in the step of forming the multi-component self-assembled monolayer on the electrode in the production of the nucleic acid fragment-fixed electrode according to the present invention, the density of the nucleic acid fragment fixed on the surface of the multi-component self-assembled monolayer formed on the electrode is controlled by controlling the amount of the introduced bifunctional linking molecule by controlling the molar ratio of at least two components which form the multi-component self-assembled monolayer, i.e., one being a self-assembled monolayer component having a terminal reactive group which reacts with at least one of reactive groups of the bifunctional linking molecule to form a covalent bond, and the other being a self-assembled monolayer component having a terminal reactive group which does not react or has low reactivity with at least one of reactive groups of the bifunctional linking molecule.

The present invention also relates to a method of electrochemically detecting a target nucleic acid fragment which comprises the steps of contacting the nucleic acid fragment-fixed electrode to which a probe nucleic acid is fixed with a sample solution containing the target nucleic acid fragment, and hybridizing the target nucleic acid fragment to the probe nucleic acid fragment; contacting the nucleic acid fragment-fixed electrode with a molecule which has an electrochemical activity and can specifically bind to a double-strand nucleic acid formed by hybridization; and conducting an electrochemical measurement via the nucleic acid fragment-fixed electrode.

The molecule which has an electrochemical activity and can specifically bind to a double-strand nucleic acid formed is preferably an intercalater. Particularly preferably, intercalater is a threading type intercalater.

(Electrode)

The nucleic acid fragment-fixed electrode according to the present invention can preferably be produced by using the gold electrode generally used for the production of electrodes for the detection of target nucleic acid fragment which is conventionally used in electrochemical detection methods, or a variety of electrodes which have been proposed for the production of electrodes for the detection of target nucleic acid.

The electrode normally should be provided with a terminal for external output. Examples of the material of the electrode include gold, as well as precious metals such as silver, platinum, palladium and rhodium, oxides such as titanium oxide, tin oxide, manganese oxide and lead oxide, semiconductors such as Si, Ge, ZnO and CdS, and electron conductors such as titan. Gold is particularly preferably used.

The electrode used in the present invention is preferably one where a plurality of electrodes are arranged on an electrically non-conductive substrate. In this case, the electrodes are regularly arranged on the non-conductive substrate such that the electrodes do not contact with each other. For example, it is preferred to use an electrodes wherein the electrodes are regularly arranged on a plate-like substrate. Also, it is possible to use an electrode where wells (openings) having electrodes provided at the bottom surface are regularly arranged, or an electrode where bar-like substrates having electrodes provided at the top are regularly arranged.

The non-conductive substrate is preferably an electrically insulating hydrophobic support, or an electrically insulating low-hydrophilic support. A substrate having coarse and non-flat surface may also be preferably used. Examples of the material of the substrate include glass, cement, ceramics or new ceramics, polyethylene terephthalate, acetylcellulose, polycarbonate of bisphenol-A, polystyrene, polymers such as polymethyl methacrylate, silicone, activated carbon, and porous material such as porous glass, porous ceramics, porous silicone, porous activated carbon, woven or textile fabric, non-woven fabric, filter paper, short fiber and membrane filter. Among them, polymers, glass and silicon are particularly preferable for reasons of easiness of the surface treatment and electrochemical analysis. The thickness of the substrate is not particularly limited but is preferably in the range of from 100 to 10000 µm in the case of a plate-like substrate.

As the example where a plurality of electrodes are arranged on a non-conductive substrate, it is preferred to treat the non-conductive substrate surface with the above-mentioned electron conductive materials. It is particularly preferred that gold is evaporated on the surface. The substrate may be provided with a layer of hydrophilic polymeric substance having electric charges or a layer of crosslinking agent prior to the surface treatment with electron conductor. By providing these layers, the coarseness of the substrate can be reduced. In some substrates, a hydrophilic polymeric substance having electric charges may be contained therein, and a substrate subjected to such a treatment may also be preferably employed.

As examples where a plurality of electrodes are arranged on a non-conductive substrate, a silicon chip known from Sosnowski, R. G. et al., Proc. Natl. Acid. Sci. U.S.A., 94, 1119-1123, 1997, may be preferably used. Alternatively, electrodes may be printed on the substrate as in a printed circuit board.

[Multi-component Self-assembled Monolayer]

The multi-component self-assembled monolayer in the nucleic acid fragment-fixed electrode according to the present invention is self-assembled monolayers (SAMs) which is composed of at least two components having different reactive groups. The self-assembled monolayer is known to be a monolayer having a high orientation, which is typically formed on the surface of gold by the interaction of alkyl long-chains, when an alkanethiol compound is contacted with the gold surface and allowed to stand while the alkanethiol is reacted with the gold surface to thereby form an Au—S bond. The self-assembled monolayer is utilized in surface plasmon resonance (SPR) and quartz crystal microbalance (QCM), for example.

The multi-component self-assembled monolayer in the nucleic acid fragment-fixed electrode according to the present invention may be a self-assembled monolayer formed not only by components having a thiol group (—SH) but also by components having a disulfide group (—S—S—) or a sulfide group (—S—) as the linking groups to the electrode. Also, the electrode may preferably comprise not only gold but also metals such as silver, platinum and copper, a variety of semiconductors, and oxides.

By thus forming the self-assembled monolayer on the electrode, the bifunctional linking molecule can be stably introduced without being directly influenced by the condition of the electrode surface. Further, the stable introduction of the bifunctional linking molecule onto the self-assembled monolayer surface formed on the electrode allows the nucleic acid fragment to be stably fixed via the bifunctional linking molecule.

One important aspect of the self-assembled monolayer in the nucleic acid fragment-fixed electrode according to the present invention is that the layer is a self-assembled monolayer composed of multiple components. That is, the layer is formed of at least two components, i.e., component 1 having a reactive group at a terminal (opposite the linking group to the electrode) which reacts with at least one of reactive groups of the bifunctional linking molecule to form a covalent bond, and component 2 having a reactive group at a terminal (opposite the linking group to the electrode) which does not react or has low reactivity with either reactive group of the bifunctional linking molecule.

By thus forming the self-assembled monolayer with multiple components having different reactivities with respect to the reactive group of the bifunctional linking molecule, the amount (density) of the bifunctional linking molecules which are introduced into the surface of the multi-component self-assembled monolayer can be controlled. Namely, by controlling the molar ratio of components 1 and 2 which form the multi-component self-assembled monolayer, the existing amount (density) of the reactive groups in the surface of the multi-component self-assembled monolayer that react with the reactive groups of the bifunctional linking molecules to thereby form a covalent bond can be controlled, so that the amount (density) of the bifunctional linking molecules that are introduced can be controlled. Specifically, in order to control the molar ratio of components 1 and 2 which form the multi-component self-assembled monolayer, the molar ratio of components 1 and 2 in the solution that is brought into contact with the electrode surface during the formation of the multi-component self-assembled monolayer is controlled.

The molar ratio of components 1 and 2 in the solution which is contacted with the electrode surface during the formation of the multi-component self-assembled monolayer should preferably be in the range of from 1:1 to 1:1000, more preferably from 1:2 to 1:500.

By controlling the amount (density) of the bifunctional linking molecules which are introduced into the surface of the multi-component self-assembled monolayer, it becomes possible to control the amount (density) of the nucleic acid fragment which is fixed to the surface of the multi-component self-assembled monolayer via the bifunctional linking molecules. Because the amount (density) of the nucleic acid fragments fixed on the electrode affects the easiness of hybridization with the target nucleic acid fragment and therefore determines the detection sensitivity and limitations, controlling of the amount is extremely important for practical purposes.

In the prior art, in order to control the amount (density) of the nucleic acid fragments which are fixed on the electrode, the concentration of the nucleic acid fragment in the solution of the fixed nucleic acid fragment which is to be directly brought into contact with the surface of the electrode is controlled. In this technique, there was the problem that sufficiently high reproducibility could not be obtained when the amount (density) of the nucleic acid fragments that are fixed on the electrode was lowered (i.e., when the concentration of the nucleic acid fragment in the solution of the fixed nucleic acid fragment is lowered). In the method according to the present invention, however, the amount of fixed nucleic acid fragment can be freely controlled with high reproducibility by simply controlling the molar ratio of the components (components 1 and 2) of the multi-component self-assembled monolayer.

FIG. 1 schematically illustrates the concept of the present invention wherein the amount (density) of the nucleic acid fragment to be fixed on the surface of the multi-component self-assembled monolayer via the bifunctional linking molecule is controlled by controlling the amount (density) of the bifunctional linking molecules which are introduced onto the surface of the multi-component self-assembled monolayer.

An example of the multi-component self-assembled monolayer in the nucleic acid fragment-fixed electrode according to the present invention is a multi-component self-assembled monolayer which is composed of at least two components represented by the following formula (1) with the type of J″ being different:

  (1)

wherein q″ represents a group which is chemically bound to or adsorbed on the electrode, R″ represents s a linking group, J″ represents different functional groups of n types, and n represents an integer of 2 or more, and in the components of formula (1) of n types, q″ and R″ may be identical or different from each other, and J″ are different from each other.

q″ represents a group which is chemically bound to or adsorbed on the electrode. Examples thereof include thiol group (—SH), disulfide group (—S—S—), and sulfide group (—S—).

R″ represents a linking group, preferably that of a hydrocarbon group such as a hydrocarbon group having 3 to 16 carbon atoms.

J″ represents different functional groups of n types, and at least one type thereof is a reactive group which forms a covalent bond with $X^1$ of formula (2).

In a preferred embodiment of the present invention, the multi-component self-assembled monolayer is composed of at least two different components represented by the following formula (4):

  (4)

wherein $q^1$ represents a group which is chemically bound to or adsorbed on the electrode, $R^1$ represents a linking group, $J^1$ represents a reactive group which forms a covalent bond with the reactive group $X^1$ in the above formula (2); and the following formula (5):

  (5)

wherein $q^2$ represents a group which is chemically bound to or adsorbed on the electrode, $R^2$ represents a linking group, and $J^2$ represents a functional group which does not react or has low reactivity with the reactive groups $X^1$ and $X^2$ in the above formula (2).

$q^1$ and $q^2$ are as described with regard to q″, and $R^1$ and $R^2$ are as described with regard to R″.

Examples of the reactive group representd by $J^1$ which forms a covalent bond with the reactive group $X^1$ of formula (2) include amino group (—NH$_2$), imino group (═NH), hydrazino group (—NHNH$_2$), carbamoyl group (—OCNH$_2$), and hydrazinocarbonyl group (—CONHNH$_2$).

Examples of the functional group representd by $J^2$ which does not react or has low reactivity with the reactive groups $X^1$ and $X^2$ of formula (2) include hydroxyl group (—OH), carboxyl group (—COOH), methyl group (—CH$_3$) and phenyl group (—C$_6$H$_5$).

In the case where the electrode is formed by gold and the bifunctional linking molecule is a disulfone compound described later, as a preferred example of the multi-component self-assembled monolayer in the nucleic acid fragment-fixed electrode according to the present invention, it is preferred to use at least two components, i.e., an alkanethiol (having 3 to 16 carbon atoms) having a terminal amino group and an alkanethiol (having 3 to 16 carbon atoms) having a terminal hydroxyl group, as comments which form the multi-component self-assembled monolayer.

When the multi-component self-assembled monolayer in the nucleic acid fragment-fixed electrode according to the present invention is formed, a static voltage can be preferably applied to the electrode surface. By applying a static voltage to the electrode surface, it becomes possible to form a more densely packed multi-component self-assembled monolayer on the electrode. In this case, the static voltage applied to the electrode surface is preferably in the range of from −10 to −500 mV.

(Bifunctional Linking Molecule)

Examples of the bifunctional linking molecule used for producing the nucleic acid fragment-fixed electrode according to the present invention include those represented by the following formula (2):

$$X^1\text{-}L^1\text{-}X^2 \quad (2)$$

wherein $X^1$ represents a reactive group which forms a covalent bond with at least one type of the functional group $J''$ in the above formula (1), $X^2$ represents a reactive group which forms a covalent bond with a functional group Z in the following formula (3), and $L^1$ represents a linking group.

Particularly preferred bifunctional linking molecules are disulfone compounds represented by the following formula (6):

$$X^1\text{---}SO_2\text{-}L^3\text{-}SO_2\text{---}X^2 \quad (6)$$

wherein $X^1$ and $X^2$ represent independently $-CR^1=CR^2R^3$ or $-CHR^1-CR^2R^3Y$ (a reactive precursor group); $R^1$, $R^2$ and $R^3$ represent independently an atom or a group selected from the group consisting of a hydrogen atom, an alkyl group having 1 to 6 carbon atoms, an aryl group having 6 to 20 carbon atoms, and an aralkyl group having 7 to 26 carbon atoms in total which has an alkyl chain having 1 to 6 carbon atoms; Y represents an atom or a group selected from the group consisting of a halogen atom, $-OSO_2R^{11}$, $-OCOR^2$, $-OSO_3M$ and quaternary pyridinium group; $R^{11}$ represents a group selected from the group consisting of an alkyl group having 1 to 6 carbon atoms, an aryl group having 6 to 20 carbon atoms, and an aralkyl group having 7 to 26 carbon atoms in total which has an alkyl chain having 1 to 6 carbon atoms; $R^{12}$ represents a group selected from the group consisting of an alkyl group having 1 to 6 carbon atoms, and a halogenated alkyl group having 1 to 6 carbon atoms; M represents an atom or a group selected from the group consisting of a hydrogen atom, alkaline metal atom and ammonium group; and $L^3$ represents a linking group.

Examples of the disulfone compound preferably used in the present invention are described below. Two or more types of disulfone compounds may be mixed.

$$H_2C=CH\text{---}SO_2\text{---}CH_2\text{---}SO_2\text{---}CH=CH_2 \quad (S1)$$

$$H_2C=CH\text{---}SO_2\text{---}CH_2OCH_2\text{---}SO_2\text{---}CH=CH_2 \quad (S2)$$

$$H_2C=CH\text{---}SO_2\text{---}CH_2CH_2CH_2\text{---}SO_2\text{---}CH=CH_2 \quad (S3)$$

$$H_2C=CH\text{---}SO_2\text{---}CH_2CH(OH)CH_2\text{---}SO_2\text{---}CH=CH_2 \quad (S4)$$

$$H_2C=CH\text{---}SO_2\text{---}CH_2CONHCH_2CH_2NHCOCH_2\text{---}SO_2\text{---}CH=CH_2 \quad (S5)$$

$$H_2C=CH\text{---}SO_2\text{---}CH_2CONHCH_2CH_2NHCOCH_2\text{---}SO_2\text{---}CH=CH_2 \quad (S6)$$

(S7)

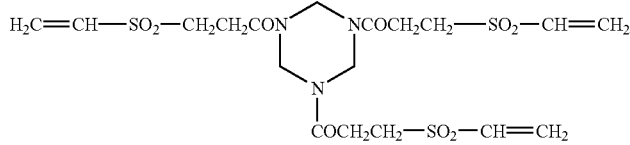
(S8)

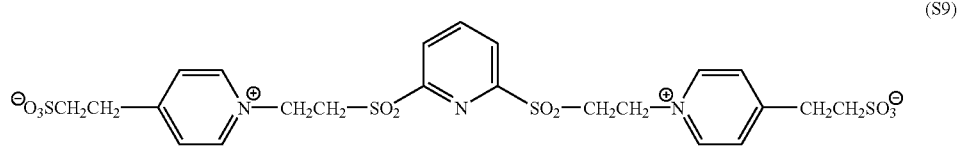
(S9)

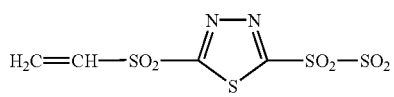
(S10)

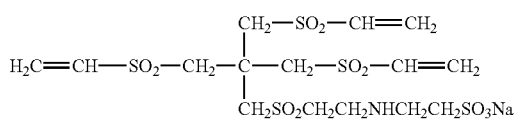
(S11)

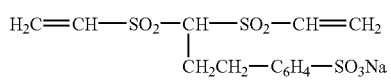
(S12)

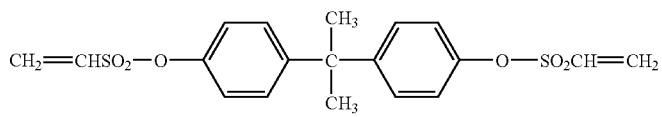
(S13)

-continued

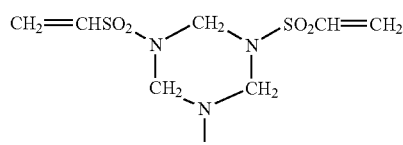
(S14)

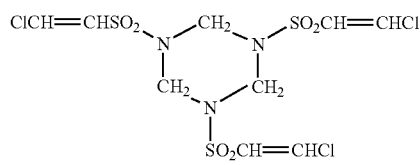
(S15)

A typical example of the disulfone compounds represented by the above formula (6) is 1,2-bis(vinylsulfonylacetamide)ethane (which corresponds to $S^1$ mentioned above).

The details of the method of synthesizing the disulfone compound used in the present invention are known from Japanese Patent Examined Publication (kokoku) Nos. 47-2429 and 50-35807, Japanese Patent Application Laid-Open (kokai) Nos. 49-24435, 53-41551, and 59-18944, for example.

(Nucleic Acid Fragment to be Fixed)

In the nucleic acid fragment-fixed electrode according to the present invention, a nucleic acid fragment which is bound and fixed to the surface of the multi-component self-assembled monolayer via the bifunctional linking molecule is preferably a nucleic acid fragment which is modified at the terminal with a reactive group which reacts with at least one of the reactive groups of the bifunctional linking molecule to thereby form a covalent bond.

In particular, when the bifunctional linking molecule is a disulfone compound represented by the above formula (6), a nucleic acid fragment modified at the terminal with an amino group (—$NH_2$) can be advantageously used. When the nucleic acid fragment is a DNA fragment, a DNA fragment whose terminal is modified with an amino group via a linking group can be used. When the nucleic acid fragment is a PNA, a PNA fragment in which lysine (Lys) residue is introduced at terminus can be used.

In the prior art, when a nucleic acid fragment is to be fixed to the electrode surface, the nucleic acid fragment modified at the terminal with a thiol group (—SH) is used. However, there was the problem that the thiol groups at the modified terminals of the nucleic acid fragment react with each other in the solution to form a disulfide (—S—S—), thereby dimerizing the nucleic acid fragment and resulting in a poor reproducibility of the fixing reaction. In the method of fixing the nucleic acid fragment to the electrode according to the present invention, a nucleic acid fragment modified at the terminal with an amino group (—$NH_2$) can be used, so that the fixing reaction can be advantageously performed in a stable manner.

(Intercalater Having an Electrochemical Activity)

The intercalater used in the method of detecting hybridization of the probe nucleic acid fragment on the DNA chip to the target nucleic acid fragment by electrochemical measurements may be of any type as long as it has an electrochemical activity and can specifically bind to the double-stranded nucleic acid. Preferably, a threading type intercalater such as disclosed in Japanese Patent Laid-Open (kokai) No. 9-288080 and J. Chem. Soc. Commun., 1111 (1998) is advantageously used.

The intercalater represented by the following formula (18) can also be preferably used. The intercalater of the formula (18) is characterized in that it has a peak current value in the range of between 400 to 600 mV of applied voltage.

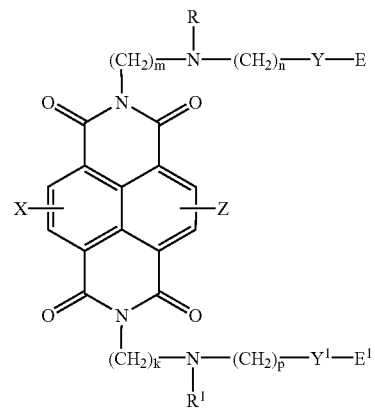
(18)

In the above formula (18), the N-substituted imino group is a group which provides solubility to the threading type intercalater. R and $R^1$ represent independently an atom or group selected from the group consisting of a hydrogen atom, and alkyl group having 1 to 3 carbon atoms, acyl group having 2 to 4 carbon atoms, aryl group which has 6 to 20 carbon atoms, and aralkyl group having 7 to 23 carbon atoms which has an alkyl group having 1 to 3 carbon atoms, each of which may have a substituent. The alkyl group having 1 to 3 carbon atoms is preferably a methyl group or an ethyl group, particularly preferably a methyl group. The acyl group having 2 to 4 carbon atoms is preferably an acetyl group. The aryl group having 6 to 20 carbon atoms is preferably a phenyl group or a naphthyl group, particularly preferably a phenyl group. The aralkyl group having 7 to 23 carbon atoms which has an alkyl group having 1 to 3 carbon atoms is preferably a benzyl group. R and R1 are preferably identical atoms or groups, and particularly preferably a methyl group.

The substituent is an atom or a group selected from the group consisting of a hydroxyl group, halogen atom (F, Cl, Br, and the like), carboxyl group, alkyl group having 1 to 6 carbon atoms, alkylamino group having 1 to 6 carbon atoms, halogenated alkyl group having 1 to 6 carbon atoms, aryl group having 6 to 12 carbon atoms, and alkoxy group having 1 to 6 carbon atoms. The number of the substituents is preferably in the range of from 1 to 12, more preferably 1 to 3, and most preferably 1, for the alkyl group having 1 to 6 carbon atoms, alkylamino group having 1 to 6 carbon atoms, halogenated alkyl group having 1 to 6 carbon atoms, and alkoxy group having 1 to 6 carbon atoms. For the aryl group having 6 to 12 carbon atoms, the number is preferably in the range of from 1 to 7, more preferably from 1 to 3, and most preferably 1.

Y and $Y^1$ represent independently —NH—CO-group or —CO—NH-group, preferably —NH—CO-group. The carbonyl group or imino group of these groups binds to E and $E^1$, respectively.

E and $E^1$ represent independently a ferrocene having a single bond. The ferrocene may or may not have a substituent. When it has a substituent, the substituent is preferably identical. Examples of the ferrocene having a substituent are shown below. The position of the substituent may be any position of the cyclopentadienyl group.

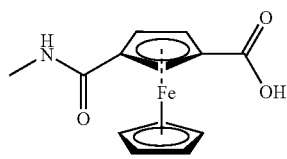
(X1)

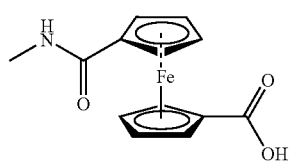
(X2)

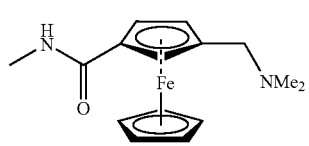
(X3)

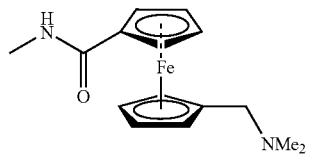
(X4)

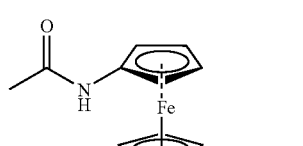
(X5)

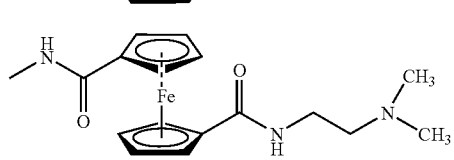
(X6)

X and Z represent independently a hydrogen atom, a halogen atom, or an alkyl group having 1 to 6 carbon atoms, preferably a hydrogen atom. Preferred examples of the alkyl group having 1 to 6 carbon atoms are the same as for the above-mentioned R (or $R^1$).

m, n, k and p determine the length of the linker portion of the threading type intercalater, and each represents an integer from 1 to 6. The sum of m and n and that of k and p, are from 4 to 8. Preferably, m and k, and n and p are the same number, respectively. Most preferably, m, n, k and p are all 3.

The aforementioned threading type intercalater having an electrochemical activity can be easily produced with good yields by the method described in Japanese Patent Application Laid-Open (kokai) No. 9-288080, for example.

For the detection of the target nucleic acid fragment by using the nucleic acid fragment-fixed electrode according to the present invention, the threading type intercalater having an electrochemical activity represented by the following formula (19) is preferably used. The intercalater represented by the formula (19) is characterized in that it has a peak current value in the range of from 100 to 400 mV of the applied voltage.

$$E_a\text{-}L_a\text{-}X\text{-}L_b\text{-}E_b \qquad (19)$$

wherein $E_a$ and $E_b$ represent independently a group which shows an oxidation-reduction activity and contains a conjugated system, X represents a bivalent cyclic group, and $L_a$ and $L_b$ represent independently a linking group which do not form a conjugated system by which the conjugated system of $E_a$ and $E_b$ are extended, at least one of which is a linking group which has a site that imparts water solubility to the present compound or has a site which can be converted into a water-solubility imparting site.

In formula (19), it is preferable that $E_a$ and $E_b$, and $L_a$ and $L_b$ are identical groups, respectively. Further, the number of atoms which constitutes a shortest linking path between the backbone chains of the linking portions represented by $L_a$-X-$L_b$ is preferably in the range of from 10 to 100, more preferably from 15 to 70, and most preferably from 20 to 50. When the calculation of the number of atoms which constitutes the shortest linking path between the backbone chains of the linking portions is applied to the above-mentioned ferrocene carboxylate N-hydroxysuccinimido ester, the number of atoms turns out to be 32.

Preferably, $E_a$ and $E_b$ are independently an oxidation-reduction active groups selected from the group consisting of metallocene having one or more bonds, 2,2'-bipyridine complex, cyclobutadiene complex, cyclopentadienyl complex, 1,10-phenanthroline complex, triphenylphosphine complex, catecholamine, and viologen, each of which may have a substituent.

The compound of the formula (19) is preferably a compound represented by the following formula (20):

$$E_a\text{-}L_{1a}\text{-}L_{2a}\text{-}X\text{-}L_{2b}\text{-}L_{1b}\text{-}E_b \qquad (20)$$

wherein $E_a$ and $E_b$ represent independently a group having an oxidation-reduction activity and containing a conjugated system, $L_{1a}$ and $L_{1b}$ represent independently a group which does not form a conjugated system by which the conjugated system of $E_a$ and $E_b$ is extended, $L_{2a}$ and $L_{2b}$ represent independently a linking group which has a site that imparts water solubility or has a site that can be converted into a water-solubility imparting site, and X represents a bivalent cyclic group.

Preferably, $L_{1a}$ and $L^{1b}$ are independently a hydrocarbon group which may have a substituent, particularly an alkylene group having 1 to 6 carbon atoms which may have a substituent, or an alkenylene group having 1 to 6 carbon atoms which may have a substituent.

Preferably, $L_{2a}$ and $L_{2b}$ are independently a linking group containing an element other than carbon element (e.g., N, O, and S), particularly a linking group containing a group selected from the group consisting of an amide linking group, ester linking group, ether linking group, thioether linking group, diimide linking group, thiodiimide linking group, thioamide linking group, imino linking group, carbonyl linking group, thiocarbonyl linking group, and 1,4-piperazinyl group, each of which may have a substituent. Most preferable is —NHCO-group or —CONH-group. $E_a$ and $E_b$, $L_{1a}$ and $L_{1b}$, and $L_{2a}$, and $L_{2b}$ are advantageously respectively identical groups.

By using the threading type intercalater of the formulae (19) and (20), a relatively low electric potential in the range of from 100 to 400 mV can be used as the potential to be applied to the electrode substrate during the detection of the nucleic acid fragment.

In the formulae (19) and (20), X represents a bivalent cyclic group which may have a substituent. The bivalent cyclic group preferably is a planar cyclic group, and is preferably selected from the group consisting of a naphthalene diimide group having bonding sites at its two nitrogen atoms, an anthracene group having bonding sites at 2-and 6-positions or 1- and 5-positions (preferably 2- and 6-positions), an anthraquinone group having bonding sites in the same manner as in the anthracene group, a fluorene group having bonding sites at 2- and 6-positions, a biphenylene group having bonding sites at 2- and 6-positions, a phenanthrene group having bonding sites at 2- and 7-positions, and a pyrene group having bonding sites at 2- and 7-positions. Particularly preferable is a naphthalene diimide group having bonding sites at the two nitrogen atoms. The substituent is preferably a hydrogen atom, a halogen atom (such as F, Cl, or Br), or an alkyl group having 1 to 6 carbon atoms, and particularly preferably a hydrogen atom. The alkyl group having 1 to 6 carbon atoms is preferably methyl group, ethyl group, or n-propyl group.

In formula (19), $L_a$ and $L_b$ represent independently a linking group which do not form a conjugated system by which the conjugated system of $E_a$ and $E_b$ are extended, at least one of which is a linking group which has a site that imparts water solubility to the present compound or has a site which can be converted into a water-solubility imparting site. The "site which can be converted into a water-solubility imparting site" has a site, such as an imino group having a methyl group as a substituent, which can be converted into a sulfate site upon contact with an acid such as sulfuric acid, thereby showing water solubility. Of course, "a site that imparts water solubility to the present compound" may have a charged portion such as a salt portion.

Preferably, $L_a$ and $L_b$ are independently a linking group which have, on the side adjacent to $E_a$ and $E_b$, a hydrocarbon group (corresponding to $L_{1a}$ and $L_{1b}$ in formula (20)) which may have a substituent, and which, on the side adjacent to X, have a linking group (corresponding to $L_{2a}$ and $L_{2b}$ in formula (20)) which contains an element other than the carbon element Thus, $L_a$ and $L_b$ are preferably a linking group corresponding to the -$L_{1a}$-$L_{2a}$- and -$L_{2b}$-$L_{1b}$- in formula (20), respectively. Preferably, $L_{1a}$ and $L_{1b}$ are independently an alkylene group having 1 to 6 carbon atoms which may have a substituent, or an alkenylene group having 2 to 6 carbon atoms which may have a substituent. Preferably, $L_{1a}$ and $L_{2b}$ are independently a linking group containing N, O, or S.

The substituent of $L_{1a}$ and $L_{1b}$ is an atom or a group selected from the group consisting of hydroxyl group, halogen atom, carboxyl group, amino group, cyano group, nitro group, formyl group, formylamino group, alkyl group having 1 to 6 carbon atoms, alkylamino group having 1 to 6 carbon atoms, halogenated alkyl group having 1 to 6 carbon atoms, cycloalkylamino group having 5 to 7 carbon atoms, dialkylamino group having 2 to 12 carbon atoms, aryl group having 6 to 12 carbon atoms, aralkyl group having 7 to 18 carbon atoms which has an alkyl group having 1 to 6 carbon atoms, aralkylamino group having 7 to 18 carbon atoms which has an alkyl group having 1 to 6 carbon atoms, alkanoyl group having 2 to 7 carbon atoms, alkanoylamino group having 2 to 7 carbon atoms, N-alkanoyl-N-alkylamino group having 3 to 10 carbon atoms, aminocarbonyl group, alkoxycarbonyl group having 2 to 7 carbon atoms, heterocyclic group having 2 to 10 carbon atoms containing 1 to 4 heteroatoms selected from the group consisting of S, N and O, and aryl group having 6 to 12 ring-constituting carbon atoms which may have, as a substituent, 1 to 5 of an alkyl group having 1 to 6 carbon atoms, an alkoxy group having 1 to 6 carbon atoms or halogen atom. The number of the substituents is preferably in the range of from 1 to 12, more preferably from 1 to 3, in the case of an alkylene group having 1 to 6 carbon atoms. The number of substituents is preferably in the range of from 1 to 10, more preferably from 1 to 3, in the case of an alkenylene group having 1 to 6 carbon atoms.

Preferably, $L_{2a}$ and $L_{2b}$ are independently a linking group containing one or more groups selected from the group consisting of an amide linking group, ester linking group, ether linking group, thioether linking group, diimide linking group, thiodiimide linking group, thioamide linking group, imino linking group, carbonyl linking group, thiocarbonyl linking group, and 1,4-piperadinyl group, each of which may have a substituent. Particularly preferable is an amide group (—NHCO-group or —CONH— group).

Examples of the substituents in $L_{2a}$ and $L_{1b}$ include those selected from the group consisting of an alkyl group having 1 to 3 carbon atoms, acyl group having 2 to 4 carbon atoms, aryl group having 6 to 20 carbon atoms, and aralkyl group having 7 to 23 carbon atoms which has an alkyl group having 1 to 3 carbon atoms. The alkyl group having 1 to 3 carbon atoms is preferably methyl group or ethyl group, and more preferably methyl group. The acyl group having 2 to 4 carbon atoms is preferably acetyl group. The aryl group having 6 to 20 carbon atoms is preferably phenyl group or naphthyl group, more preferably phenyl group. The aralkyl group having 7 to 23 carbon atoms which has an alkyl group having 1 to 3 carbon atoms is preferably a benzyl group.

When $L_{2a}$ and $L_{2b}$ are imino linking groups, the substituent is preferably methyl group. Preferably, $L_{2a}$ and $L_{2b}$ are independently an N-methyl-di(n-propylenyl)imino group or 1,4-di(n-propylenyl)-piperazinyl group. Most preferred is N-methyl-di(n-propylenyl)imino group.

$E_a$ and $E_b$ are a group which has an oxidation-reduction activity and imparts an electric conductivity, and each may have independently a substituent. Preferable examples include metallocene having one or more bonds, 2,2'-bipyridine complex, cyclobutadiene complex, cyclopentadienyl complex, 1,10-phenanthroline complex, triphenylphosphine complex, catecholamine, and viologen. Particularly preferable is a ferrocene having a single bond which may have a substituent. $E_a$ and $E_b$ are preferably an identical group with each other. Examples of the ferrocene having a substituent are shown below. The position of the substituent may be any position of the cyclopentadienyl group.

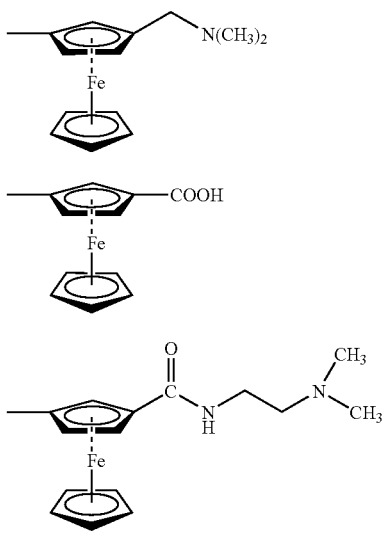

(F1), (F2), (F3)

The compounds which can be advantageously used as the threading type intercalater of the formulae (19) and (20) can be easily produced by a known producing method (Japanese Patent Application Laid-Open (kokai) No. 9-288080) by using a known diamine compound as the starting material.

The compound of the formulae (19) and (20) can be also produced cheaply and with good yields by a synthesis route represented by the following formula using a known diamine compound as the starting material.

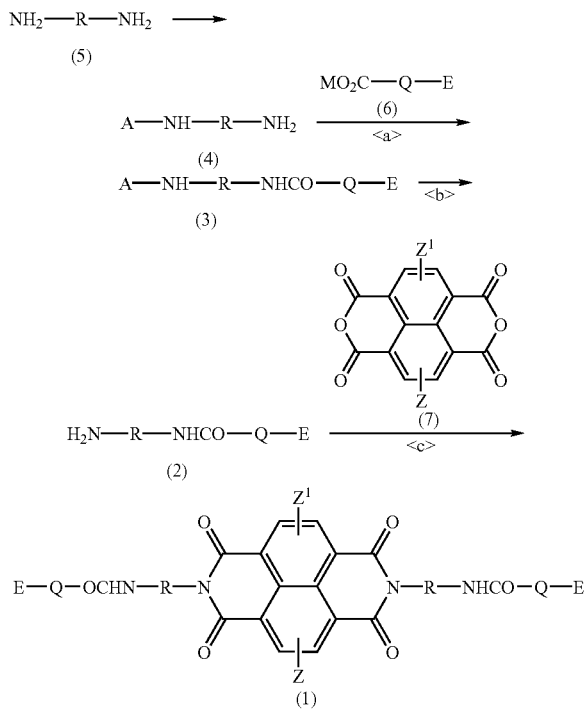

(Electrochemical Measurement)

Electrochemical measurement can be performed by any method as long as the amount of current can be measured via the nucleic acid fragment-fixed electrode according to the present invention. Preferably, cyclic voltammography (CV), differential pulse voltammography (DPV), linear sweep voltammography, potentiostat or the like is used.

EXAMPLES

The present invention will be described below by the following examples, but the present invention is not limited to those examples.

Example 1

Production of a DNA Fragment Fixed Electrode According to the Present Invention, and Electrochemical Detection of a Sample DNA Fragment Using the Electrode (1) Production of a DNA Fragment (Probe) Fixed Electrode A gold electrode with an area of 1.0 mm$^2$ was dipped into a mixed ethanol solution of 6-amino-1-hexanethiol (0.014 mM) and 6-hydroxy-1-hexanethiol (1 mM) and left to stand at 45° C. for 8 hours. The electrode surface was then washed five times with ethanol at 40° C. for 10 minutes each time, followed by washing five times by an ultrapure water-ethanol mixed solution (1:1) at 40° C. for 10 minutes each. The surface was further washed three times with ultrapure water at 40° C. for 10 minutes each, thereby sufficiently removing the components which did not bind to the gold electrode surface and obtaining an electrode on the surface of which a self-assembled monolayer composed of the two components, i.e., 6-amino-1-hexanethiol and 6-hydroxy-1-hexanethiol, were formed. The electrode having the thus formed self-assembled monolayer was then dipped into a phosphoric acid buffer solution (pH 8.5) of 3% 1,2-bis (vinylsulfonylacetamide)ethane, and left to stand at room temperature for 2 hours. Thereafter, the electrode surface was washed with distilled water at 25° C. for 10 minutes, thereby obtaining a reactive gold electrode having a vinyl-sulfonyl group at the free terminal on the self-assembled monolayer. Then, onto the surface of this reactive gold electrode was dropped 2 μL of an aqueous solution (0.1 μM) of DNA fragment of the following nucleotide sequence (partial nucleotide sequence of the ALDH-2 gene) which is modified with an aminohexyl group at 5'-terminal. After allowing to stand at room temperature for 1 hour, the electrode surface was washed with ultrapure water at 25° C. for 10 minutes, and then dried, thereby obtaining the DNA fragment fixed electrode according to the present invention.

<Sequence of the Fixed DNA Fragment>
(5'-terminal→3'-terminal):
CAGGCATACACTGAAGTGAAAACTG (SEQ ID NO: 1)

(2) Preparation of a Sample DNA Fragment (Target)

A sample nucleic acid fragment was prepared by PCR using a reaction solution of the composition shown below. PCR was conducted by repeating 30 cycles, each cycle being composed of denaturation at 94° C. for 30 seconds, annealing at 65° C. for 30 seconds, and polymerase elongation reaction at 72° C. for 1 minute.

23

<Composition of the Reaction Solution>

| | |
|---|---|
| Purified water | 36.5 μL |
| 10 × PCR buffer | 5 μL |
| 2.5 mM dNTP | 4 μL |
| TaqFP (Nippon Gene) | 0.5 μL |
| 20 μM primer | 2 μL |
| 30 ng/μL target nucleic acid fragment sample solution | 2 μL |

As the primer, Primer 1 (forward primer) and Primer 2 (reverse primer) were used which contained the nucleotide sequence of the DNA fragment fixed to the electrode and were designed so as to amplify a part of ALDH-2 gene as a nucleic acid of 280 base pairs.

<Sequence of the Primer>

Primer 1

(5'-terminal→3'-terminal): ATTACAGGGTCAACTGC-TATG (SEQ ID NO: 2)

Primer 2

(5'-terminal→3'-terminal): AGGTCCTGAACTTCCAG-CAG (SEQ ID NO: 3)

(3) Electrochemical Detection of the Sample DNA Fragment by Using the DNA Fragment Fixed Electrode According to the Present Invention

[Measurement of Background]

The DNA fragment fixed electrode according to the invention prepared in (1) was dipped in a 0.1M potassium chloride/0.1M acetic acid buffer solution (pH 5.6) at 20° C. containing 50 μM of a ferrocene-modified, electrochemically active threading type intercalater represented by the following formula (21), and differential pulse voltammetry (DPV) measurement was conducted in the range of from 100 to 700 mV of the applied voltage. The response current value (background value) at the applied voltage of 260 mV was determined, and it was found to be −0.6 μA. The DPV measurement was conducted with a pulse amplitude 50 mV, a pulse width 50 mS, and a scan speed 100 mV/s.

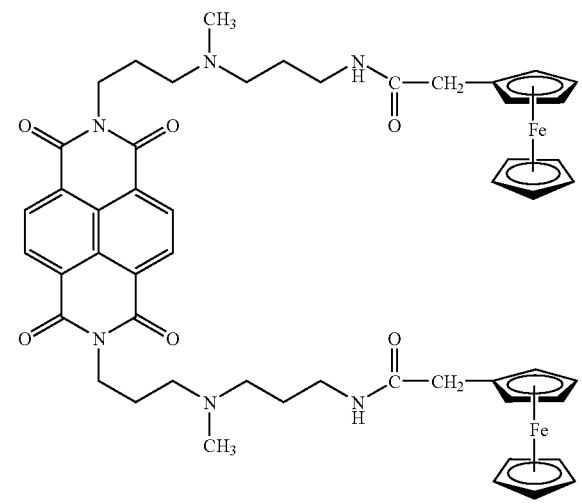

(21)

24

[Hybridization]

A solution (0.5% SDS, 5×SSC) containing the sample DNA fragment ($10^{-8}$M) obtained in (2) was heated at 95° C. for 2 minutes and then cooled with ice to obtain a hybridization solution. The hybridization solution was brought into contact with the DNA fixed electrode of the present invention produced in (1), and incubation was carried out at 60° C. for 2 hours in a manner such that the hybridization solution did not dry. The surface of the DNA modified electrode after incubation was washed with a 25° C. 5×SSC to thereby remove unreacted sample DNA fragments. Thereafter, the same operation as in the above measurement of the background value was conducted to measure the response current value after hybridization of the DNA fragment (probe) fixed on the electrode to the sample DNA fragment (target), and the value was found to be −3.2 μA. The rate of change of the response current value after hybridization to the background value was 433%.

(4) Evaluation of Measurement Reproducibility

The production of the DNA fragment fixed electrode in the above operation (1) and the electrochemical detection of the sample nucleic acid fragment by using the DNA fragment fixed electrode in operation (3) were performed on 10 individual gold electrodes, to thereby determine the measurement reproducibility in 10 DNA fragment fixed electrodes (N=10) in terms of a variation factor CV (%) of the rate of change after hybridization to the measured value of background. As a result, CV was 8.6%.

Comparative Example 1

Electrochemical Detection of the Sample DNA Fragment by Using the Conventional DNA Fragment Fixed Electrode (1) Production of a Conventional DNA Fragment Fixed Electrode 2 μL of an aqueous solution (0.1 pM) of a DNA fragment which has the same nucleotide sequence as that of the DNA fragment fixed on the electrode surface in Example 1 and has a mercaptohexyl group at the 5'-terminal was dropped on a gold electrode having an area of 1.0 mm². The electrode was allowed to stand for 1 hour at room temperature, and then the electrode surface was washed with ultrapure water at 25° C. for 10 minutes and dried, thereby obtaining a DNA fragment fixed electrode in which the DNA fragment was directly fixed on the surface of a conventional gold electrode.

(2) Electrochemical Detection of the Sample DNA Fragment by Using the Conventional DNA Fragment Fixed Electrode The same procedures for the measurement of background, preparation of hybridization solution, hybridization operation and post-hybridization measurement as in Example 1 were performed except for the use of the DNA fragment fixed electrode prepared in (1). The background measurement value, the post-hybridization measurement value, and the rate of change were −1.6 μA, −3.0 μA, and 88%, respectively.

(3) Evaluation of Reproducibility

Measurement reproducibility (N=10) was determined with respect to 10 individual gold electrodes according to the method described in Example 1 except that the DNA fixed gold electrode produced by the operation (1) to which the DNA fragment was directly fixed on the conventional gold electrode surface was used, and CV was found to be 18.6%.

Based on the results of Example 1 and Comparative Example 1, it can be understood that the sample DNA fragment (target) can be detected with higher S/N (signal to noise) ratio and better reproducibility by using the DNA fragment fixed electrode according to the present invention, as compared with the case of using the DNA fragment fixed electrode according to the prior art.

Example 2

Production of the PNA Fragment Fixed Electrode According to the Present Invention and Electrochemical Detection of a Sample DNA Fragment by Using the Electrode (1) Production of the PNA Fragment (Probe) Fixed Electrode A gold electrode with an area of 1.0 mm$^2$ was dipped into a mixed ethanol solution of 6-amino-1-hexanethiol (0.014 mM) and 6-hydroxy-1-hexanethiol (1 mM) and left to stand at 45° C. for 8 hours. The electrode surface was then washed five times with ethanol at 40° C. for 10 minutes each time, followed by washing five times by an ultrapure water-ethanol mixed solution (1:1) at 40° C. for 10 minutes each. The surface was further washed three times with ultrapure water at 40° C. for 10 minutes each, thereby sufficiently removing the components which did not bind to the gold electrode surface and obtaining an electrode on the surface of which a self-assembled monolayer composed of the two components, i.e., 6-amino-1-hexanethiol and 6-hydroxy-1-hexanethiol, were formed. The electrode having the thus formed self-assembled monolayer was then dipped into a phosphoric acid buffer solution (pH 8.5) of 3% 1,2-bis(vinylsulfonylacetamide)ethane, and left to stand at room temperature for 2 hours. Thereafter, the electrode surface was washed with distilled water at 25° C. for 10 minutes, thereby obtaining a reactive gold electrode having a vinylsulfonyl group at the free terminal on the self-assembled monolayer. Then, onto the surface of this reactive gold electrode was dropped 2 μL of an aqueous solution (0.1 pM) of PNA fragment of the following nucleotide sequence which has a lysine (Lys) residue at the N terminal. After allowing to stand at room temperature for 1 hour, the electrode surface was washed with ultrapure water at 25° C. for 10 minutes, and then dried, thereby obtaining the PNA fragment fixed electrode according to the present invention.

<Sequence of the Fixed PNA Fragment>
(N-terminal→C-terminal): Lys-GATTAGCAGTCTACG (SEQ ID NO: 4)

(2) Preparation of the Sample DNA Fragment (Target)

A solution (5×SSC) containing a DNA fragment (10$^{-8}$M) having a nucleotide sequence complimentary to that of the PNA fragment fixed on the electrode as a probe in (1) was prepared as a hybridization solution.

<Sequence of the Sample DNA Fragment>
(5'-terminal→3'-terminal): CGTAGACTCCTAAGC (SEQ ID NO: 5)

(3) Electrochemical Detection of the Sample DNA Fragment by Using the PNA Fixed Electrode According to the Present Invention The same procedures for the background measurement, hybridization operation, and post-hybridization measurement as in Example 1, except for the use of the PNA fixed gold electrode prepared in (1) and the hybridization solution prepared in (2), were employed to determine the background measurement value, post-hybridization measurement value, and the rate of change. As a result, they were found to be −0.5 μA, −2.0 μA, and 300%, respectively.

(3) Evaluation of Reproducibility

Measurement reproducibility (N=10) was determined with respect to 10 individual gold electrodes according to the same method as described in Example 1 except for the use of the PNA fragment fixed gold electrode according to the present invention prepared by the above operation (1). CV was found to be 9.6%.

Based on the result of Example 2, it can be understood that the sample DNA fragment (target) can be detected with higher S/N (signal/noise) ratio and with better reproducibility by using the PNA fragment fixed electrode according to the present invention.

Example 3

Control of the Amount of the DNA Fragment Fixed on the Electrode Reference Example 1

(1) Fixing of a Fluorescent Pigment (Cy Pigment) Labeled DNA Fragment (Present Invention)

A set of 10 gold electrodes with an area of 1.0 mm$^2$ each was dipped into each of ethanol solutions of 6-amino-1-hexanethiol and 6-hydroxy-1-hexanethiol with mixture ratios of 1:7, 1:70 and 1:700. After allowing to stand at 45° C. for 8 hours, the surface of each of the electrodes was washed five times with ethanol at 40° C. for 10 minutes each time. The surface was further washed five times with ultrapure water-ethanol mixture (1:1) solution at 40° C. for 10 minutes each time, and further washed three times with ultrapure water at 40° C. for 10 minutes each time, thereby sufficiently removing the components that did not bind to the gold electrode surface and obtaining three sets of 10 electrodes on which a self-assembled monolayer was formed, each set having a different ratio of the components of 6-amino-1-hexanethiol and 6-hydroxy-1-hexanethiol. Thereafter, all of the electrodes having the self-assembled monolayer formed thereon were dipped into a phosphoric acid buffer solution (pH 8.5) of 3% 1,2-bis(vinylsulphonylacetomide)ethane and allowed to stand at room temperature for 2 hours. The electrode surface was then washed with distilled water at 25° C. for 10 minutes, thereby obtaining three sets of 10 reactive gold electrodes having a vinylsulfonyl group at the free terminal on the self-assembled monolayer, with different ratios of the components of 6-amino-1-hexanethiol and 6-hydroxy-1-hexanethiol. Onto the surface of the reactive gold electrodes was then dropped 2 μL of an aqueous solution (0.1 pM) of a DNA fragment of the following nucleotide sequence in which the 5'-terminal is modified with an aminohexyl group and the 3'-terminal is labeled with a fluorescent dye (Cy dye). After allowing to stand at room temperature for 1 hour, the electrode surface was washed with ultrapure water at 25° C. for 10 minutes and then dried, thereby obtaining three sets of ten electrodes on which the DNA fragment labeled with the fluorescent dye (Cy dye) was fixed, each set having a different ratio of the components of 6-amino-1-hexanethiol and 6-hydroxy-1-hexanethiol.

<Sequence of the Fixed DNA Fragment>
(5'-terminal→3'-terminal):
CAGGCATACACTGAAGTGAAAACTG (SEQ ID NO: 6)

(2) Measurement of Fluorescence Intensity

The fluorescence intensity on the surface of the electrodes produced in (1) having the multi-component self-assembled monolayer formed thereon with the mixture ratios of 1:7, 1:70 and 1:700 of 6-amino-1-hexanethiol and 6-hydroxy-1-hexanethiol, each electrode having the fluorescent dye (Cy dye) labeled DNA fragment fixed thereon, was measured by a laser scanning apparatus. The fluorescence intensity that is measured here corresponds to the amount of the DNA fragment which is fixed on the electrode surface.

A mean fluorescence intensity value and its variation coefficient CV (%) were determined for each set of 10 electrodes with mixture ratios 1:7, 1:70 and 1:700 of 6-amino-1-hexanethiol and 6-hydroxy-1-hexanethiol. The mean values were 28500, 16000 and 2400, respectively, and the variation coefficients were 2.3%, 2.8% and 3.2%, respectively.

Comparative Example 2

Control of the Amount of the DNA Fragment Fixed on the Electrode Reference Example 2

(1) Fixing of a Fluorescent Dye (Cy Dye) Labeled DNA Fragment (According to Prior Art)

Aqueous solutions of a DNA fragment which has the same nucleotide sequence as that of the DNA fragment fixed on the electrode surface and labeled with the fluorescent dye (Cy dye) in Example 3, and which has a mercaptohexyl group at the 5'-terminal and is labeled with the fluorescent dye (Cy dye) at the 3'-terminal, were prepared with DNA fragment concentrations of 1 pM, 0.1 pM and 0.01 pM. 2 µL each of the solutions was dropped on a group of 10 gold electrodes with an area of 1.0 mm² each, and the electrodes were allowed to stand at room temperature for 1 hour. The electrode surface was then washed with ultrapure water at 25° C. for 10 minutes and then dried, thereby obtaining gold electrodes on the surface of which the fluorescent dye (Cy dye) labeled DNA fragment was directly fixed.

(2) Measurement of Fluorescence Intensity

The fluorescence intensity on the surface of the electrodes was measured in the same manner as in Example 3, the electrodes having been prepared in (1) by using the aqueous solutions of the fluorescent pigment (Cy dye) labeled DNA fragment with the concentrations of 1 pM, 0.1 pM and 0.01 pM and having fixed thereon the fluorescent dye (Cy dye) labeled DNA fragment. The mean value of the fluorescent intensity and the coefficient of variation (%) were thereby determined for each set of 10 electrodes prepared by using the aqueous solutions of the fluorescent dye (Cy dye) labeled DNA fragment with the concentrations of 1 pM, 0.1 pM and 0.01 pM. The mean values were 8500, 3400 and 800, respectively, and the variation coefficients were 13.5%, 18.6% and 25.6%, respectively.

Based on the results of Example 3 and Comparative Example 2, it can be udderstood that the amount of the DNA fragment fixed on the electrode can be controlled with better reproducibility by using the method according to the present invention, as compared with the conventional method.

Example 4

Control of the Amount of the DNA Fragment Fixed on the Electrode Commensurate With the Concentration of the Sample DNA Fragment (1) Preparation of the DNA Fragment Fixed Electrode A gold electrode with an area of 1.0 mm² was dipped into each of ethanol solutions of 6-amino-1-hexanethiol and 6-hydroxy-1-hexanethiol with mixture ratios of 1:7, 1:70 and 1:700. After allowing to stand at 45° C. for 8 hours, the surface of each electrode was washed five times with ethanol at 40° C. for 10 minutes each, and then five times with an ultrapure water-ethanol mixture (1:1) solution at 40° C. for 10 minutes each. The electrode surface was further washed three times with ultrapure water at 40° C. for 10 minutes each, thereby sufficiently removing the components that did not bind to the gold electrode surface and obtaining electrodes on which a self-assembled monolayer was formed with different ratios of the components of 6-amino-1-hexanethiol and 6-hydroxy-1-hexanethiol. The electrodes having the self-assembled monolayer were then all dipped into a phosphoric acid buffer solution (pH 8.5) of 3% 1,2-bis (vinylsulfonylacetamide)ethane. After allowing to stand at room temperature for 2 hours, the electrode surface was washed with distilled water at 25° C. for 10 minutes, thereby obtaining reactive electrodes having a vinylsulfonyl group at the free terminal on the self-assembled monolayer with different ratios of the components of 6-amino-1-hexanethiol and 6-hydroxy-1-hexanethiol. Onto the surface of these reactive gold electrodes was then dropped 2 µL of an aqueous solution (0.1 pM) of a DNA fragment identical to the one used in Example 1 and modified at the 5'-terminal with an aminohexyl group. After allowing to stand at room temperature for 1 hour, the electrode surface was washed with ultrapure water at 25° C. for 10 minutes and then dried, thereby obtaining electrodes on which the DNA fragment was fixed, with different ratios of the components of 6-amino-1-hexanethiol and 6-hydroxy-1-hexanethiol.

(2) Electrochemical Detection of the Sample DNA Fragment by Using the DNA Fragment Fixed Electrode The same method as described in Example 1 was used to perform background measurement, hybridization operation, and post-hybridization measurement, except that, for the individual DNA fragment fixed electrodes prepared in (1) with different ratios of the components of 6-amino-1-hexanethiol and 6-hydroxy-1-hexanethiol, there were provided hybridization solutions prepared by heating solutions (0.5% SDS, 5×SSC) of the sample DNA fragment obtained in (2) of Example 1 with concentrations of $10^{-11}$M, $10^{-10}$M, $10^{-9}$M, $10^{-8}$M, $10^{-7}$M, and $10^{-6}$M at 95° C. for two minutes and then cooling them with ice. Table 1 shows the background measurement values and the ratios of change (%) calculated on the basis of the post-hybridization measurement values.

It can be understood from Table 1 that the range in which the rate of change (%) well depends on the concentration of the sample DNA fragment, differs depending on the ratio of the components of 6-amino-1-hexanethiol and 6-hydroxy-1-hexanethiol. That is, the range in which the rate of change (%) corresponds well to the concentration of the sample DNA fragment is from $10^{-9}$M to $10^{-6}$M when the component ratio of 6-amino-1-hexanethiol and 6-hydroxy-1-hexanethiol is 1:7, from $10^{-10}$M to $10^{-7}$M with the component ratio 1:70, and from $10^{-11}$M to $10^{-8}$M with the component ratio 1:700.

TABLE 1

| DNA fragment<br>DNA fragment fixed electrode | Concentration of sample | | | | | |
|---|---|---|---|---|---|---|
| | $10^{-11}$ | $10^{-10}$ | $10^{-9}$ | $10^{-8}$ | $10^{-7}$ | $10^{-6}$ |
| | Ratio of Change (%) | | | | | |
| 1:7 | 0 | 0 | 28 | 135 | 513 | 523 |
| 1:70 | 0 | 10 | 123 | 433 | 483 | 490 |
| 1:700 | 33 | 240 | 365 | 410 | 405 | 423 |

1:7, 1:70 and 1:700 represents a component ratio of 6-amino-1-hexanethiol:6-hydroxy-1-hexanethiol.

The results in Table 1 show that, by changing the ratio of the components (6-amino-1-hexanethiol and 6-hydroxy-1-hexanethiol) which form the multi-component self-assembled monolayer, the amount (density) of the bifunctional linking molecules introduced onto the surface of the multi-component self-assembled monolayer changes, thereby changing the amount (density) of the DNA fragments fixed on the surface of the multi-component self-assembled monolayer via the bifunctional linking molecule.

This shows that the nucleic acid fragment-fixed electrode according to the present invention can be designed in such a way that the detection concentration range is optimized depending on the concentration of the sample nucleic acid fragment.

Example 5

Detection of Single Nucleotide Polymorphisms (SNPs) of an Aldehyde Dehydrogenase Gene (ALDH-2 Gene) by Using the DNA Fragment Fixed Electrode According to the Present Invention (1) Preparation of a DNA Fragment (Probe) Fixed Electrode A gold electrode with an area of 1.0 mm² was dipped into a mixed ethanol solution of 6-amino-1 hexanethiol (0.014 mM) and 6-hydroxy-1-hexanethiol (1 mM), and was then allowed to stand for 8 hours at 45° C. The electrode surface was then washed five times with ethanol at 40° C. for 10 minutes. The surface was further washed five times with ultrapure water-ethanol mixture solution (1:1) at 40° C. for 10 minutes, and then three times by ultrapure water at 40° C. for 10 minutes, thereby sufficiently removing the components that did not bind to the gold electrode surface and obtaining an electrode on whose surface a self-assembled monolayer consisting of the two components of 6-amino-1-hexanethiol and 6-hydroxy-1-hexanethiol was formed. The electrode having the self-assembled monolayer formed thereon was then dipped into a phosphoric acid buffer solution (pH 8.5) of 3% 1,2-bis(vinylsulfonylacetamide) ethane, and was then allowed to stand at room temperature for 2 hours. The electrode surface was thereafter washed with distilled water at 25° C. for 10 minutes, thereby obtaining a reactive gold electrode having a vinylsulfonyl group at the free terminal on the self-assembled monolayer. On the surface of the reactive gold electrode was then dropped 2 µL each of aqueous solutions (0.1 pM) of DNA fragments of the following nucleotide sequences, i.e., the two nucleotide sequences (a) and (b) each having a different nucleotide sequence at a specific portion on the ALDH-2 gene that determines the activity of ALDH-2, which is modified at 5'-terminal with an aminohexyl group. After allowing to stand at room temperature for 1 hour, the electrode surface was washed with ultrapure water at 25° C. for 10 minutes and then dried, thereby obtaining DNA fragment fixed electrodes (a) and (b) of the present invention for determining the nucleotide sequence (SNPs) of the sample DNA fragment.

<Sequence of the Fixed DNA Fragment>
(a): (5'-terminal→3'-terminal):
CAGGCATACACTGAAGTGAAAACTG (SEQ ID NO: 7)
(b): (5'-terminal→3'-terminal):
CAGGCATACACTAAAGTGAAAACTG (SEQ ID NO: 8)

(As to the underlined nucleotide sequences, the sample DNA fragment has a nucleotide sequence complementary to (a) when the sample DNA fragment is of an active ALDH-2, and has a nucleotide sequence complementary to (b) in the case of an inactive ALDH-2.)

(2) Preparation of the Sample DNA Fragment (Target)

A genomic nucleic acid fragment was extracted and purified by using commercially available nucleic acid extraction and purification kit (QIAamp DNA Blood Mini Kit from QIAGEN) from blood samples collected from several human subjects, and nucleic acid fragments were recovered in 1 mL of purified and distilled water. Genomic nucleic acid fragments were then subjected to PCR using a reaction solution of the following composition. PCR was conducted by repeating 30 cycles, each cycle being composed of denaturation at 94° C. for 30 seconds, annealing at 65° C. for 30 seconds, and polymerase elongation reaction at 72° C. for 1 minute.

<Composition of the Reaction Solution>

| | |
|---|---|
| Purified water | 36.5 µL |
| 10 × PCR buffer | 5 µL |
| 2.5 mM dNTP | 4 µL |
| Taq FP (produced by Nippon Gene) | 0.5 µL |
| 20 µM primer | 2 µL |
| 30 ng/µL target nucleic acid fragment sample solution | 2 µL |

As primers, Primer 1 (forward primer) and Primer 2 (reverse primer) were used which comprised the nucleotide sequence of the DNA fragment fixed to the electrode and which were designed to amplify a part of the ALDH-2 gene as a 280-base pair nucleic acid.

<Sequences of the Primers>
Primer 1: (5'-terminal→3'-terminal):
ATTACAGGGTCAACTGCTATG (SEQ ID NO:9)
Primer 2: (5'-terminal→3'-terminal):
AGGTCCTGAACTTCCAGCAG (SEQ ID NO:10)

The nucleotide sequence of the portion amplified by the above PCR was determined by ABI-3700 sequencer (Applied Biosystems), and one nucleotide sequence determined to be of the active ALDH-2 and one nucleotide sequence determined to be the inactive ALDH-2 were used as sample DNA fragments.

(3) Electrochemical Detection of the Sample DNA Fragments Using the DNA Fragment Fixed Electrode The same method as described in Example 1 was used for background measurement, preparation of hybridization solutions, hybridization operation and post-hybridization measurement, except for the use of the DNA fragment fixed electrode prepared in (1) and the sample DNA fragments prepared in (2). Based on background measurement values and post-hybridization measurement values, the rate of change (%) was calculated. The rates of change were, respectively for the active ALDH-2 and the inactive ALDH-2 of the sample DNA fragment, 433(%) and 86(%) in the DNA fragment fixed electrode (a) (magnitude of rate of change: active>inactive), and 74(%) and 429(%) in the DNA fragment fixed electrode (2) (magnitude of rate of change: active<inactive). Thus, the difference in the nucleotide sequences of the sample DNA fragments was detected in the form of a difference in magnitude of the detection values.

The results of Example 5 show that single nucleotide polymorphisms (SNPs) of the aldehyde dehydrogenase gene (ALDH-2 gene) can be detected by using the DNA fragment fixed electrode according to the present invention. Thus, single nucleotide polymorphisms (SNPs) on genomic nucleic acids can be detected by using the DNA fragment fixed electrode according to the present invention.

INDUSTRIAL APPLICABILITY

As described above, the present invention provides a nucleic acid fixed electrode wherein a probe nucleic acid fragment is fixed on the electrode in a stable and amount-(density-) controlled manner, as well as a method of producing the electrode.

```
                        SEQUENCE LISTING

<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: Sequence of the fixed DNA fragment; Partial
      nucleotide sequence of the ALDH-2 gene which is modified with an
      aminohexyl group at the 5'-terminal end

<400> SEQUENCE: 1
caggcataca ctgaagtgaa aactg                                        25

<210> SEQ ID NO 2
<211> LENGTH: 21
<212> TYPE: DNA
<213> ORGANISM: Artificial Sequence
<220> FEATURE:
<223> OTHER INFORMATION: Forward primer designed to amplify part of
      the ALDH-2 gene

<400> SEQUENCE: 2
attacagggt caactgctat g                                            21

<210> SEQ ID NO 3
<211> LENGTH: 20
<212> TYPE: DNA
<213> ORGANISM: Artificial Sequence
<220> FEATURE:
<223> OTHER INFORMATION: Reverse primer designed to amplify part of the
      ALDH-2 gene

<400> SEQUENCE: 3
aggtcctgaa cttccagcag                                              20

<210> SEQ ID NO 4
<211> LENGTH: 15
<212> TYPE: DNA
<213> ORGANISM: Artificial Sequence
<220> FEATURE:
<223> OTHER INFORMATION: Nucleic acid sequence of the fixed peptide
      nucleic acid (PNA) fragment; The PNA fragment contains a Lysine
      residue at the N-terminal

<400> SEQUENCE: 4
gattagcagt ctacg                                                   15

<210> SEQ ID NO 5
<211> LENGTH: 15
<212> TYPE: DNA
<213> ORGANISM: Artificial Sequence
```

```
<220> FEATURE:
<223> OTHER INFORMATION: Sequence of the sample DNA fragment;
      Complimentary to the PNA fragment of SEQ ID NO: 4

<400> SEQUENCE: 5
cgtagactcc taagc                                                    15

<210> SEQ ID NO 6
<211> LENGTH: 25
<212> TYPE: DNA
<213> ORGANISM: Artificial Sequence
<220> FEATURE:
<223> OTHER INFORMATION: Sequence of the fixed DNA fragment; The 5'
      -terminal is modified with an aminohexyl group and the 3'
      -terminal is labeled with a fluorescent dye (Cy dye)

<400> SEQUENCE: 6
caggcataca ctgaagtgaa aactg                                         25

<210> SEQ ID NO 7
<211> LENGTH: 25
<212> TYPE: DNA
<213> ORGANISM: Artificial Sequence
<220> FEATURE:
<223> OTHER INFORMATION: Sequence of the fixed DNA fragment; Partial
      nucleotide sequence of the ALDH-2 gene which is modified with an
      aminohexyl group at the 5'-terminal end

<400> SEQUENCE: 7
caggcataca ctgaagtgaa aactg                                         25

<210> SEQ ID NO 8
<211> LENGTH: 25
<212> TYPE: DNA
<213> ORGANISM: Artificial Sequence
<220> FEATURE:
<223> OTHER INFORMATION: Sequence of the fixed DNA fragment; Partial
      nucleotide sequence of the ALDH-2 gene which is modified with an
      aminohexyl group at the 5'-terminal end

<400> SEQUENCE: 8
caggcataca ctaaagtgaa aactg                                         25

<210> SEQ ID NO 9
<211> LENGTH: 21
<212> TYPE: DNA
<213> ORGANISM: Artificial Sequence
<220> FEATURE:
<223> OTHER INFORMATION: Forward primer designed to amplify part of
      the ALDH-2 gene

<400> SEQUENCE: 9
attacagggt caactgctat g                                             21

<210> SEQ ID NO 10
<211> LENGTH: 20
<212> TYPE: DNA
<213> ORGANISM: Artificial Sequence
<220> FEATURE:
<223> OTHER INFORMATION: Reverse primer designed to amplify part of the
      ALDH-2 gene

<400> SEQUENCE: 10
aggtcctgaa cttccagcag                                               20
```

What is claimed is:

1. An electrode assembly, comprising:
   an electrode;
   a multi-component self-assembled monolayer of two or more different components formed on the electrode; and
   a nucleic acid fragment fixed on the surface of the monolayer by a covalent bond via a bifunctional linking molecule, wherein said bifunctional linking molecules does not comprise a nucleic acid, and
wherein the monolayer is composed of at least two components represented by the following formula (1) with the type of $J''$ being different:

$$q''\text{-}R''\text{-}J'' \tag{1}$$

wherein $q''$ represents a group which is chemically bound to or adsorbed on the electrode, $R''$ represents a linking group, $J''$ represents different functional groups of n types, and n represents an integer of 2 or more, and in the components of formula (1) of n types, $q''$ and $R''$ may be identical or different from each other, and $J''$ are different from each other;
wherein the bifunctional linking molecule is represented by the following formula (2):

$$X^1\text{-}L^1\text{-}X^2 \tag{2}$$

wherein $X^1$ represents a group which forms a covalent bond with at least one type of the functional group $J''$ in the above formula (1), $X^2$ represents a group which forms a covalent bond with a functional group Z in the following formula (3), and $L^1$ represents a linking group; and
   wherein the nucleic acid fragment is represented by the following formula (3):

$$Z\text{-}L^2\text{-}Nc \tag{3}$$

wherein Z represents a group which forms a covalent bond with the group $X^2$ in the above formula (2), Nc represents a nucleic acid fragment, and $L^2$ represents a linking group.

2. The electrode assembly according to claim 1, wherein the multi-component self-assembled monolayer formed on the electrode is composed of at least two different components, wherein
   at least one component is represented by the following formula (4):

$$q^1\text{-}R^1\text{-}J^1 \tag{4}$$

wherein $q^1$ represents a group which is chemically bound to or adsorbed on the electrode, $R^1$ represents a linking group, $J^1$ represents a group which forms a covalent bond with the group $X^1$ in the above formula (2); and
   at least one component by the following formula (5):

$$q^2\text{-}R^2\text{-}J^2 \tag{5}$$

wherein $q^2$ represents a group which is chemically bound to or adsorbed on the electrode, $R^2$ represents a linking group, and $J^2$ represents a functional group which does not react or has low reactivity with the groups $X^1$ and $X^2$ in the above formula (2).

3. The electrode assembly according to claim 1, wherein the electrode is made of gold.

4. The electrode assembly according to claim 1, wherein the multi-component self-assembled monolayer comprises
   (A) an alkanethiol having a terminal amino group and having 3 to 16 carbon atoms, and
   (B) an alkanethiol having a terminal hydroxyl group and having 3 to 16 carbon atoms.

5. The electrode assembly according to claim 1, wherein the bifunctional linking molecule is a disulfone compound represented by the following formula (6):

$$X^1\text{---}SO_2\text{-}L^3\text{-}SO_2\text{---}X^2 \tag{6}$$

wherein
   $X^1$ and $X^2$ represent independently $-CR^1{=}CR^2R^3$ or $-CHR^1{-}CR^2R^3Y$;
   $R^1$, $R^2$ and $R^3$ represent independently an atom or a group selected from the group consisting of a hydrogen atom, an alkyl group having 1 to 6 carbon atoms, an aryl group having 6 to 20 carbon atoms, and an aralkyl group having 7 to 26 carbon atoms in total which has an alkyl chain having 1 to 6 carbon atoms;
   Y represents an atom or a group selected from the group consisting of a halogen atom, $-OSO_2R^{11}$, $-OCOR^{12}$, $-OSO_3M$ and quaternary pyridinium group;
   $R^{11}$ represents a group selected from the group consisting of an alkyl group having 1 to 6 carbon atoms, an aryl group having 6 to 20 carbon atoms, and an aralkyl group having 7 to 26 carbon atoms in total which has an alkyl chain having 1 to 6 carbon atoms;
   $R^{12}$ represents a group selected from the group consisting of an alkyl group having 1 to 6 carbon atoms, and a halogenated alkyl group having 1 to 6 carbon atoms;
   M represents an atom or a group selected from the group consisting of a hydrogen atom, alkaline metal atom and ammonium group; and
   $L^3$ represents a linking group.

6. The electrode assembly according to claim 1, wherein the nucleic acid fragment is either a DNA fragment modified at a terminal with an amino acid group, which is represented by the following formula (7):

$$NH_2\text{-}L^4\text{-}DNA \tag{7}$$

wherein $L^4$ represents a linking group; or
   a PNA fragment having a terminal lysine residue, which is represented by the following formula (8):

$$\text{Lys-PNA} \tag{8}$$

wherein Lys represents a lysine residue.

7. A method for producing an electrode assembly wherein a nucleic acid fragment is fixed on the surface of a multi-component self-assembled monolayer of two or more different components which is formed on the electrode, by a covalent bond via a bifunctional linking molecule, the method comprising at least the steps of:
   (a) forming a multi-component self-assembled monolayer on an electrode by contacting the electrode with at least two components represented by the following formula (1) with the type of $J''$ being different:

$$q''\text{-}R''\text{-}J'' \tag{1}$$

wherein $q''$ represents a group which is chemically bound to or adsorbed on the electrode, $R''$ represents a linking group, $J''$ represents different functional groups of n types, and n represents an integer of 2 or more, and in the components of formula (1) of n types, $q''$ and $R''$ may be identical or different from each other, and $J''$ are different from each other; and then removing the components which were not chemically bound to or adsorbed on the electrode;
   (b) introducing a group $X^2$ onto the surface of the multi-component self-assembled monolayer by contacting the electrode obtained in step (a) on which the multi-component self-assembled monolayer is formed with a bifunctional linking molecule represented by the following formula (2):

$$X^1\text{-}L^1\text{-}X^2 \tag{2}$$

wherein said bifunctional linking molecule does not comprise a nucleic acid, and wherein $X^1$ represents a group which forms a covalent bond with at least one type of functional group $J''$ in the above formula (1), $X^2$ represents a group which forms a covalent bond with a functional group Z in the following formula (3), and $L^1$ represents a linking group; and then removing the components which did not form a covalent bond with the reactive group $J''$ on the multi-component self-assembled monolayer; and (c) binding a nucleic acid fragment partially to the surface of the multi-component self-assembled monolayer by contacting the electrode obtained in step (b) having a multi-component self-assembled monolayer on which the group $X^2$ is introduced with a nucleic acid fragment represented by the following formula (3):

$$Z\text{-}L^2\text{-}Nc \tag{3}$$

wherein Z represents a group which forms a covalent bond with the group $X^2$ in the above formula (2), Nc represents a nucleic acid fragment, and $L^2$ represents a linking group; and then removing the unwanted components which did not form a covalent bond with the group $X^2$ introduced onto the multi-component self-assembled monolayer.

8. The method according to claim 7, wherein, in the step of forming the multi-component self-assembled monolayer on the electrode, the multi-component self-assembled monolayer is formed on the electrode by contacting the electrode with a mixture solution containing at least two different components, wherein at least one component is represented by the following formula (4):

$$q^1\text{-}R^1\text{-}J^1 \tag{4}$$

wherein $q^1$ represents a group which is chemically bound to or adsorbed on the electrode, $R^1$ represents a linking group, $J^1$ represents a group which forms a covalent bond with the group $X^1$ in the above formula (2); and at least one component is represented by the following formula (5):

$$q^2\text{-}R^2\text{-}J^2 \tag{5}$$

wherein $q^2$ represents a group which is chemically bound to or adsorbed on the electrode, $R^2$ represents a linking group, and $J^2$ represents a functional group which does not react or has low reactivity with the groups $X^1$ and $X^2$ in the above formula (2); and then removing the components which were not chemically bound to or adsorbed on the electrode; and further the group $X^2$ is partially introduced onto the surface of the multi-component self-assembled monolayer by contacting the electrode with the bifunctional linking molecule of the above formula (2) and then removing the components which did not form a covalent bond with the group $J''$ on the multi-component self-assembled monolayer.

9. The method according to claim 8, wherein the amount of the nucleic acid fragment bound via the bifunctional linking molecule to the surface of the multi-component self-assembled monolayer formed on the electrode is controlled by changing the molar ratio of the molecule ($q^1$-$R^1$-$J^1$) represented by formula (4) and the molecule ($q^2$-$R^2$-$J^2$) represented by formula (5) in the mixture solution which is brought into contact with the electrode.

10. The method according to claim 8, wherein the molar ratio of the molecule ($q^1$-$R^1$-$J^1$) represented by formula (4) and the molecule ($q^2$-$R^2$-$J^2$) represented by formula (5) in the mixture solution to be contacted with the electrode is in the range of from 1:1 to 1:1000.

11. The method according to claim 7, wherein the electrode is made of gold.

12. The method according to claim 8, wherein the molecule ($q^1$-$R^1$-$J^1$) represented by formula (4) is an alkanethiol having a terminal amino group and having 3 to 16 carbon atoms, and the molecule ($q^2$-$R^2$-$J^2$) represented by formula (5) is an alkanethiol having a terminal hydroxyl group and having 3 to 16 carbon atoms.

13. The method according to claim 7, wherein the bifunctional linking molecule is a disulfone compound represented by the following formula (6):

$$X^1\text{—}SO_2\text{-}L^3\text{-}SO_2\text{—}X^2 \tag{6}$$

wherein $X^1$ and $X^2$ represent independently —$CR^1$=$CR^2R^3$ or —$CHR^1$—$CR^2R^3Y$;

$R^1$, $R^2$ and $R^3$ represent independently an atom or a group selected from the group consisting of a hydrogen atom, an alkyl group having 1 to 6 carbon atoms, an aryl group having 6 to 20 carbon atoms, and an aralkyl group having 7 to 26 carbon atoms in total which has an alkyl chain having 1 to 6 carbon atoms;

Y represents an atom or a group selected from the group consisting of a halogen atom, —$OSO_2R^{11}$, —$OCOR^2$, —$OSO_3M$ and quaternary pyridinium group;

$R^{11}$ represents a group selected from the group consisting of an alkyl group having 1 to 6 carbon atoms, an aryl group having 6 to 20 carbon atoms, and an aralkyl group having 7 to 26 carbon atoms in total which has an alkyl chain having 1 to 6 carbon atoms;

$R^{12}$ represents a group selected from the group consisting of an alkyl group having 1 to 6 carbon atoms, and a halogenated alkyl group having 1 to 6 carbon atoms;

M represents an atom or a group selected from the group consisting of a hydrogen atom, alkaline metal atom and ammonium group; and $L^3$ represents a linking group.

14. The method according to claim 7, wherein the nucleic acid fragment is either a DNA fragment modified at the terminal with an amino acid group which is represented by the following formula (7):

$$NH_2\text{-}L^4\text{-}DNA \tag{7}$$

wherein $L^4$ represents a linking group; or a PNA fragment having a terminal lysine residue which is represented by the following formula (8):

$$Lys\text{-}PNA \tag{8}$$

wherein Lys represents a lysine residue.

* * * * *